United States Patent
Otte et al.

(10) Patent No.: US 12,242,943 B2
(45) Date of Patent: *Mar. 4, 2025

(54) GENERATING MACHINE LEARNING MODELS USING GENETIC DATA

(71) Applicant: Freenome Holdings, Inc, South San Francisco, CA (US)

(72) Inventors: Gabriel Otte, Los Altos, CA (US); Charles Roberts, London (GB); Adam Drake, Pacifica, CA (US); Riley Ennis, San Francisco, CA (US)

(73) Assignee: Freenome Holdings, Inc., South San Francisco, CA (US)

( * ) Notice: Subject to any disclaimer, the term of this patent is extended or adjusted under 35 U.S.C. 154(b) by 218 days.

This patent is subject to a terminal disclaimer.

(21) Appl. No.: 17/973,383

(22) Filed: Oct. 25, 2022

(65) Prior Publication Data
US 2023/0222311 A1   Jul. 13, 2023

Related U.S. Application Data

(63) Continuation of application No. 15/455,110, filed on Mar. 9, 2017, now Pat. No. 11,514,289.
(Continued)

(51) Int. Cl.
*G06N 3/00*   (2023.01)
*G06N 3/123*   (2023.01)
(Continued)

(52) U.S. Cl.
CPC ............... *G06N 3/00* (2013.01); *G06N 3/123* (2013.01); *G06N 20/00* (2019.01);
(Continued)

(58) Field of Classification Search
CPC .......... G06N 3/00; G06N 3/123; G06N 20/00; G06N 3/086; G06F 16/636;
(Continued)

(56) References Cited

U.S. PATENT DOCUMENTS

| | | |
|---|---|---|
| 9,663,831 B2 | 5/2017 | Apte et al. |
| 9,738,929 B2 | 8/2017 | Turner et al. |

(Continued)

FOREIGN PATENT DOCUMENTS

| | | |
|---|---|---|
| WO | 2011038507 A1 | 4/2011 |
| WO | 2012031329 A1 | 3/2012 |

(Continued)

OTHER PUBLICATIONS

U.S. Appl. No. 15/455,110, Final Office Action mailed on Feb. 24, 2021, 26 pages.
(Continued)

*Primary Examiner* — Miranda M Huang
*Assistant Examiner* — Chase P. Hinckley
(74) *Attorney, Agent, or Firm* — Kilpatrick Townsend & Stockton LLP

(57) ABSTRACT

Systems, methods, and apparatuses for generating and using machine learning models using genetic data. A set of input features for training the machine learning model can be identified and used to train the model based on training samples, e.g., for which one or more labels are known. As examples, the input features can include aligned variables (e.g., derived from sequences aligned to a population level or individual references) and/or non-aligned variables (e.g., sequence content). The features can be classified into different groups based on the underlying genetic data or intermediate values resulting from a processing of the underlying genetic data. Features can be selected from a feature space for creating a feature vector for training a model. The selection and creation of feature vectors can be performed iteratively to train many models as part of a search for optimal features and an optimal model.

27 Claims, 20 Drawing Sheets

Related U.S. Application Data

(60) Provisional application No. 62/305,976, filed on Mar. 9, 2016.

(51) Int. Cl.
    *G06N 20/00* (2019.01)
    *C12N 15/10* (2006.01)
    *C12Q 1/6806* (2018.01)
    *G06F 16/635* (2019.01)
    *G06N 3/086* (2023.01)

(52) U.S. Cl.
    CPC ...... *C12N 15/1003* (2013.01); *C12N 15/1096* (2013.01); *C12Q 1/6806* (2013.01); *C12Q 2560/00* (2013.01); *C12Q 2600/118* (2013.01); *G01N 2800/7028* (2013.01); *G06F 16/636* (2019.01); *G06N 3/086* (2013.01)

(58) Field of Classification Search
    CPC ........ G01N 2800/7028; C12N 15/1003; C12N 15/1096; C12Q 1/6806; C12Q 2560/00; C12Q 2600/118
    See application file for complete search history.

(56) References Cited

U.S. PATENT DOCUMENTS

| | | |
|---|---|---|
| 9,758,839 B2 | 9/2017 | Apte et al. |
| 10,095,831 B2 | 10/2018 | Duenwald et al. |
| 10,192,026 B2 | 1/2019 | Semenyuk |
| 10,294,532 B2 | 5/2019 | Apte et al. |
| 10,295,540 B1 | 5/2019 | Buturovic et al. |
| 10,331,849 B2 | 6/2019 | Burke et al. |
| 10,364,467 B2 | 7/2019 | Lo et al. |
| 10,415,105 B2 | 9/2019 | Apte et al. |
| 10,482,993 B2 | 11/2019 | Rava et al. |
| 10,494,675 B2 | 12/2019 | Kassis et al. |
| 10,527,624 B2 | 1/2020 | Dittamore |
| 10,563,266 B2 | 2/2020 | Velculescu et al. |
| 10,570,440 B2 | 2/2020 | White |
| 10,669,578 B2 | 6/2020 | Clarke et al. |
| 10,689,697 B2 | 6/2020 | Reid et al. |
| 10,712,334 B2 | 7/2020 | Choi et al. |
| 10,883,146 B2 | 1/2021 | Feng et al. |
| 10,900,084 B2 | 1/2021 | Goto et al. |
| 10,941,449 B2 | 3/2021 | Lapointe et al. |
| 10,982,286 B2 | 4/2021 | Kohli et al. |
| 11,035,006 B2 | 6/2021 | Schell et al. |
| 11,214,797 B2 | 1/2022 | Regev et al. |
| 11,514,289 B1 * | 11/2022 | Otte ...................... G06N 20/00 |
| 2011/0028333 A1 | 2/2011 | Christensen et al. |
| 2012/0041683 A1 | 2/2012 | Vaske et al. |
| 2012/0143805 A1 | 6/2012 | Gold et al. |
| 2012/0330566 A1 | 12/2012 | Chaisson |
| 2013/0132331 A1 | 5/2013 | Kowalczyk et al. |
| 2013/0198118 A1 | 8/2013 | Kowalczyk et al. |
| 2013/0217006 A1 | 8/2013 | Sorenson et al. |
| 2014/0121985 A1 | 5/2014 | Sayood et al. |
| 2014/0129152 A1 | 5/2014 | Beer et al. |
| 2015/0057948 A1 | 2/2015 | Reid et al. |
| 2015/0154353 A1 | 6/2015 | Xiang et al. |
| 2015/0294062 A1 | 10/2015 | Quon et al. |
| 2015/0347676 A1 | 12/2015 | Zhao et al. |
| 2015/0356242 A1 | 12/2015 | George |
| 2016/0019341 A1 | 1/2016 | Harris et al. |
| 2016/0032396 A1 | 2/2016 | Diehn et al. |
| 2016/0110515 A1 | 4/2016 | Apte et al. |
| 2016/0110584 A1 | 4/2016 | Remiszewski et al. |
| 2016/0186261 A1 | 6/2016 | Scher et al. |
| 2016/0224730 A1 | 8/2016 | Yu et al. |
| 2016/0273049 A1 | 9/2016 | Velculescu et al. |
| 2016/0281166 A1 | 9/2016 | Bhattacharjee et al. |
| 2016/0319345 A1 | 11/2016 | Gnerre et al. |
| 2016/0333416 A1 | 11/2016 | Babiarz et al. |
| 2016/0357903 A1 | 12/2016 | Shendure et al. |
| 2016/0364522 A1 | 12/2016 | Frey et al. |
| 2016/0371430 A1 | 12/2016 | Mahe et al. |
| 2017/0016054 A1 | 1/2017 | Southern et al. |
| 2017/0051358 A1 | 2/2017 | Bittinger et al. |
| 2017/0061070 A1 | 3/2017 | Kingsmore et al. |
| 2017/0061072 A1 | 3/2017 | Kermani et al. |
| 2017/0159121 A1 | 6/2017 | DeChow et al. |
| 2017/0166981 A1 | 6/2017 | Craig et al. |
| 2017/0175205 A1 | 6/2017 | Toung et al. |
| 2017/0199961 A1 | 7/2017 | Yelensky et al. |
| 2017/0204407 A1 | 7/2017 | Gilbert et al. |
| 2017/0211143 A1 | 7/2017 | Shendure et al. |
| 2017/0233804 A1 | 8/2017 | Reid et al. |
| 2017/0258854 A1 | 9/2017 | Van Den Brink et al. |
| 2017/0362638 A1 | 12/2017 | Chudova et al. |
| 2018/0018590 A1 | 1/2018 | Szeto et al. |
| 2018/0037953 A1 | 2/2018 | Emerson et al. |
| 2018/0068083 A1 | 3/2018 | Cohen et al. |
| 2018/0120291 A1 | 5/2018 | Eltoukhy et al. |
| 2018/0148778 A1 | 5/2018 | Mercer |
| 2018/0216195 A1 | 8/2018 | Elnitski et al. |
| 2018/0218789 A1 | 8/2018 | Anderson et al. |
| 2018/0251848 A1 | 9/2018 | Diehn et al. |
| 2018/0258479 A1 | 9/2018 | Aparicio et al. |
| 2018/0273911 A1 | 9/2018 | Tuller et al. |
| 2018/0322242 A1 | 11/2018 | Burke et al. |
| 2018/0327844 A1 * | 11/2018 | Deciu .................... G16B 20/00 |
| 2018/0349548 A1 | 12/2018 | Walsh et al. |
| 2018/0365375 A1 | 12/2018 | Flygare et al. |
| 2019/0025312 A1 | 1/2019 | Dittamore et al. |
| 2019/0042696 A1 | 2/2019 | Wong et al. |
| 2019/0050530 A1 | 2/2019 | De La Vega |
| 2019/0065677 A1 | 2/2019 | Gifford et al. |
| 2019/0100809 A1 | 4/2019 | Kennedy et al. |
| 2019/0169235 A1 | 6/2019 | Futcher et al. |
| 2019/0203296 A1 * | 7/2019 | Faruki .................. C12Q 1/6886 |
| 2019/0295690 A1 | 9/2019 | Gore et al. |
| 2020/0105370 A1 | 4/2020 | Troukhan et al. |
| 2020/0181710 A1 | 6/2020 | Steelman |
| 2020/0216900 A1 | 7/2020 | Bunyavanich et al. |
| 2021/0395811 A1 | 12/2021 | Garalde et al. |
| 2022/0023049 A1 | 1/2022 | Flusberg et al. |

FOREIGN PATENT DOCUMENTS

| | | |
|---|---|---|
| WO | 2014043763 A1 | 3/2014 |
| WO | 2016127944 A1 | 8/2016 |

OTHER PUBLICATIONS

U.S. Appl. No. 15/455,110, Non-Final Office Action mailed on Aug. 3, 2021, 24 pages.

U.S. Appl. No. 15/455,110, Non-Final Office Action mailed on Sep. 29, 2020, 25 pages.

U.S. Appl. No. 15/455,110, Non-Final Office Action mailed on Apr. 2, 2020, 27 pages.

U.S. Appl. No. 15/455,110, Non-Final Office Action mailed on Mar. 21, 2022, 30 pages.

U.S. Appl. No. 15/455,110, Notice of Allowance mailed on Jul. 25, 2022, 16 pages.

U.S. Appl. No. 62/268,333, Neoantigen Identification, Manufacture, and Use, filed Dec. 16, 2015, 58 pages.

U.S. Appl. No. 62/269,904, Methods, Compositions, Kits and Devices for Rapid Analysis of Biological Markers, filed Dec. 18, 2015, 262 pages.

U.S. Appl. No. 62/294,205, Third Generation Sequencing Alignment Algorithm, filed Feb. 11, 2016, 61 pages.

U.S. Appl. No. 62/387,526, Methods, Compositions, Kits and Devices for Rapid Analysis of Biological Markers, filed Dec. 23, 2015.

Achawanantakun et al., LncRNA-Id: Long Non-coding RNA Identification using Balanced Random Forests, Bioinformatics, vol. 31, No. 24, Aug. 26, 2015, pp. 3897-3905.

Ahsan, Cell Type Prediction of Transcription Factor Binding Sites Using Machine Learning, School of Computer Science, Jun. 12, 2015, 108 pages.

(56) References Cited

OTHER PUBLICATIONS

Andrychowicz et al., Learning to Learn by Gradient Descent by Gradient Descent, 30th Conference on Neural Information Processing Systems, Nov. 30, 2016, pp. 1-17.

Borozan et al., Integrating Alignment-Based and Alignment-Free Sequence Similarity Measures for Biological Sequence Classification, Sequence Analysis, vol. 31, Issue 9, May 1, 2015, pp. 1396-1404.

Boza et al., DeepNano: Deep Recurrent Neural Networks for Base Calling in MinION Nanopore Reads, PloS One, Mar. 30, 2016, pp. 1-12.

Bray et al., Near-Optimal RNA-Seq Quantification, Available Online at: https://arxiv.org/ftp/arxiv/papers/1505/1505.02710.pdf, May 15, 2015, pp. 1-21.

Chiu et al., DNAshaper: An R/Bioconductor Package For DNA Shape Prediction And Feature Encoding, Bioinformatics, vol. 32, No. 8, Dec. 14, 2015, pp. 1211-1213.

Cleary et al., Detection of Low-Abundance Bacterial Strains in Metagenomic Datasets by Eigengenome Partitioning, Nature Biotechnology, vol. 33, Issue 10, Oct. 2015, pp. 1053-1062.

Ding et al., Dectico: An Alignment-Free Supervised Metagenomic Classification Method Based on Feature Extraction and Dynamic Selection, BMC Bioinformatics, vol. 16, Issue 323, Oct. 7, 2015, pp. 1-12.

Ditzler et al., Multi-Layer and Recursive Neural Networks for Metagenomic Classification, IEEE Transactions on NanoBioscience, vol. 14, Issue 6, Sep. 2015, pp. 608-616.

Drouin et al., Learning Interpretable Models of Phenotypes from Whole Genome Sequences with the Set Covering Machine, Presented at Machine Learning in Computational Biology, arXiv:1412.1074 [q-bio.GN], Dec. 2, 2014, pp. 1-6.

Erlich, A Vision for Ubiquitous Sequencing, Genome Research, vol. 25, 2015, pp. 1411-1416.

Feurer et al., Efficient and Robust Automated Machine Learning, Advances in Neural Information Processing Systems, 2015, pp. 1-9.

Flanagan et al., DNA Methylome of Familial Breast Cancer Identifies Distinct Profiles Defined by Mutation Status, The American Journal of Human Genetics, vol. 86, No. 3, Mar. 12, 2010, pp. 420-433.

Fletez-Brant et al., Kmer-SVM: A Web Server for Identifying Predictive Regulatory Sequence Features in Genomic Data Sets, Nucleic Acids Research, vol. 41, May 17, 2013, pp. W544-W556.

Ghandi et al., Enhaced Regulatory Sequence Prediction Using Gapped k-mer Features, Plos One, Computational Biology, vol. 10, No. 7, Jul. 17, 2014, pp. 1-15.

Grechkin et al., Identifying Network Perturbation in Cancer, PLoS Computational Biology, vol. 12, No. 5, May 4, 2016, 30 pages.

Guinney et al., The Consensus Molecular Subtypes of Colorectal Cancer, Nature Medicine, vol. 21, No. 11, Nov. 2015, 13 pages.

Hafez, A Semi-Supervised Predictive Model to Link Regulatory Regions to Their Target Genes, Dissertation Duke University, Aug. 26, 2015, pp. 1-220.

Heimberg et al., Low Dimensionality in Gene Expression Data Enables the Accurate Extraction of Transcriptional Programs from Shallow Sequencing, Cell Systems, vol. 2, Apr. 27, 2016, pp. 239-250.

Hicks et al., On the Widespread and Critical Impact of Systematic Bias and Batch Effects in Single-Cell RNA-Seq Data, Available Online at: https://www.biorxiv.org/content/10.1101/025528v1.full.pdf, Aug. 25, 2015, 14 pages.

Ibrahim et al., miRNA and Gene Expression Based Cancer Classification Using Self-Learning and Co-training Approaches, IEEE International Conference on Bioinformatics and Biomedicine, Dec. 18-21, 2013, pp. 495-498.

Kamath, An Evolutionary Machine Learning Framework For Big Data Sequence Mining, Doctoral Dissertation at George Mason University, 2014, 24 pages.

Kamps et al., Next-Generation Sequencing in Oncology: Genetic Diagnosis, Risk Prediction and Cancer Classification, International Journal of Molecular Sciences, vol. 18, No. 2, Feb. 2017, 57 pages.

Kannan et al., Shannon: An Information-Optimal de Novo RNA-Seq Assembler, Available Online at: https://www.biorxiv.org/content/10.1101/039230v1.full.pdf, Feb. 1, 2016, pp. 1-14.

Klema, Machine Learning Applications in Bioinformatics, Department of Cybernetics, Faculty of Electrical Engineering, Jan. 2012, 2 pages.

Koslicki et al., WGSQuikr: Fast Whole-Genome Shotgun Metagenomic Classification, PLoS ONE, vol. 9, Issue 3, Mar. 13, 2014, pp. 1-12.

Kwon et al., NASCUP: Nucleic Acid Sequence Classification by Universal Probability, Department of Electrical and Computer Engineering, Nov. 16, 2015, 52 pages.

Lambert et al., RNA Bind-n-Seq: Measuring the Binding Affinity Landscape of RNA-Binding Proteins, Methods in Enzymology, vol. 558, 2015, pp. 465-493.

Langenkämper et al., Ake—The Accelerated K-Mer Exploration Web-Tool for Rapid Taxonomic Classification and Visualization, BMC Bioinformatics, vol. 15, No. 384, Dec. 2014, pp. 1-11.

Lapierre et al., Predicting Clinical Phenotype Using OTU-Based Metagenome Representation, IEEE International Conference on Data Mining Workshop, Nov. 2015, pp. 156-163.

Leung et al., Machine Learning in Genomic Medicine: A Review of Computational Problems and Data Sets, Proceeding of Institute of Electrical and Electronics Engineers, vol. 104, No. 1, Jan. 2016, pp. 176-197.

Li, Correcting Illumina Sequencing Errors for Human Data, Oxford University Press, Feb. 12, 2015, pp. 1-2.

Li et al., Learning 'Graph-Mer' Motifs That Predict Gene Expression Trajectories in Development, PLoS Computational Biology, vol. 6, Issue 4, Apr. 29, 2010, pp. 1-13.

Li, Minimap and Miniasm: Fast Mapping and De Novo Assembly for Noisy Long Sequences, Bioinformatics, vol. 32, No. 14, Mar. 2016, pp. 2103-2110.

Li et al., MSPKmerCounter: A Fast and Memory Efficient Approach for K-mer Counting, Department of Computer Science, May 25, 2015, pp. 1-7.

Liu et al., Identification of Microrna Precursor with The Degenerate K-Tuple or Kmer Strategy, Journal of Theoretical Biology, vol. 385, Nov. 21, 2015, pp. 153-159.

Liu et al., Using Amino Acid Physicochemical Distance Transformation for Fast Protein Remote Homology Detection, PLoS One, vol. 7, No. 9, Sep. 28, 2012, pp. 1-10.

Lopez et al., A Deep Generative Model for Single-Cell RNA Sequencing With Application to Detecting Differentially Expressed Genes, Department of Electronical Engineering and Computer Science, Oct. 18, 2017, 6 pages.

Mitra et al., Bioinformatics with Soft Computing, Institute of Electrical and Electronics Engineers, vol. 36, No. 5, Sep. 2006, pp. 616-635.

Norris et al., Nanopore Sequencing Detects Structural Variants In Cancer, Cancer Biology & Therapy, vol. 17, No. 3, Mar. 2016, pp. 246-253.

Patro et al., Accurate, Fast, and Model-Aware Transcript Expression Quantification with Salmon, Available Online at: https://www.biorxiv.org/content/10.1101/021592v2.full.pdf, Oct. 2, 2015, pp. 1-35.

Reddy, Using Machine Learning Techniques for Finding Meaningful Transcripts in Prostate Cancer Progression, University of Windsor Scholarship at UWindsor, Electronic Theses and Dissertations, Available Online At: https://pdfs.semanticscholar.org/46a9/8ce54a252d1df07cc39d85ff548140727efb.pdf?_ga=2.30694710.846928035.1598341598-1249700059.1590501170, Oct. 19, 2015, 98 pages.

Rifkin et al., An Analytical Method for Multiclass Molecular Cancer Classification, Society for Industrial and Applied Mathematics Review, vol. 45, No. 4, Dec. 2003, pp. 706-723.

Romero et al., Diet Networks: Thin Parameters for Fat Genomics, International Conference on Learning Representations, Mar. 2017, pp. 1-11.

Sato et al., Metavelvet-SL: An Extension of the Velvet Assembler to a De Novo Metagenomic Assembler Utilizing Supervised Learning, supervised learning,DNA Research,vol. 22. Issue 1, Nov. 27, 2014, pp. 69-71.

(56) References Cited

OTHER PUBLICATIONS

Setty et al., SeqGL Identifies Context-Dependent Binding Signals in Genome-Wide Regulatory Element Maps, Computational Biology Program, Memorial Sloan-Kettering Cancer Center, May 27, 2015, pp. 1-21.

Siwo et al., Prediction of Fine-tuned Promoter Activity from DNA Sequence, F1000Research, vol. 5, No. 158, Feb. 11, 2016, pp. 1-15.

Soneson et al., Differential Analyses for RNA-Seq: Transcript-Level Estimates Improve Gene-level Inferences, F1000Research, vol. 4, No. 1521, Feb. 29, 2016, pp. 1-15.

Soueidan et al., Machine Learning for Metagenomics: Methods and Tools, Bordeaux Bioinformatics Centre, Mar. 8, 2016, pp. 1-25.

Su et al., Molecular Classification of Human Carcinomas by Use of Gene Expression Signatures, Cancer Research, vol. 61, Oct. 15, 2001, pp. 7388-7393.

Subramanian et al., Reference-Free Inference of Tumor Phylogenies from Single-Cell Sequencing Data, BMC Genomics, vol. 16, No. 11, Jun. 2-4, 2014, pp. 1-11.

Suryanto et al., Protein Fold Classification Using Large Margin Combination of Distance Metrics, IEICE Transactions on Information and Systems, vol. E99.D, Issue 3, Mar. 2016, pp. 714-723.

Szalay et al., De Novo Sequencing and Variant Calling with Nanopores Using Poreseq, Nature Biotechnology, vol. 33, Oct. 2015, pp. 1087-1091.

Tan et al., Simple Decision Rules for Classifying Human Cancers from Gene Expression Profiles, Bioinformatics, vol. 21, No. 20, Oct. 15, 2005, pp. 3896-3904.

Tsai et al., Resolving the Complexity of Human Skin Metagenomes Using Single-Molecule Sequencing, mBio, vol. 7, Issue 1, Feb. 9, 2016, pp. 1-13.

Vattikuti et al., Application of Compressed Sensing to Genome Wide Association Studies and Genomic Selection, Oct. 8, 2013, pp. 1-36.

Vervier et al., Large-Scale Machine Learning for Metagenomics Sequence Classification, Bioinformatics Research Departement, May 27, 2015, pp. 1-14.

Wood et al., Kraken: Ultrafast Metagenomic Sequence Classification Using Exact Alignments, Genome Biology, vol. 15, Article No. R46, Mar. 3, 2014, pp. 1-12.

Zararsiz, Development and Application of Novel Machine Learning Approaches for RNA-Seq Data Classification, Available Online At URL: http://www.openaccess.hacettepe.edu.tr:8080/xmlui/handle/11655/998?locale-attribute=en, 2015, 138 pages.

Zeng et al., GERV: A Statistical Method for Generative Evaluation of Regulatory Variants for Transcription Factor Binding, Bioinformatics, vol. 32, No. 4, Jul. 4, 2015, pp. 1-12.

Zhai et al., Genome-Wide DNA Methylation Profiling of Cell-Free Serum DNA in Esophageal Adenocarcinoma and Barrett Esophagus, Neoplasia, vol. 14, No. 1, Jan. 31, 2012, pp. 29-33.

Zhang, Computational Analysis of Transcript Interactions and Variants in Cancer, Available Online at URL: https://conservancy.umn.edu/bitstream/handle/11299/177090/Zhang_umn_0130E_16673.pdf?sequence=1&isAllowed=y, Nov. 2015, 129 pages.

Zhang et al., Network-Based Isoform Quantification with RNA-Seq Data for Cancer Transcriptome Analysis, PLoS Computational Biology, vol. 11, No. 12, Dec. 23, 2015, 24 pages.

\* cited by examiner

- Neural nets

- Support vector machines

Spatial representation sequencing

GENERATING MACHINE LEARNING MODELS USING GENETIC DATA

CROSS-REFERENCES TO RELATED APPLICATIONS

The present application is a continuation application of U.S. patent application Ser. No. 15/455,110 entitled "GENERATING MACHINE LEARNING MODELS USING GENETIC DATA," filed on Mar. 9, 2017, which claims priority from and is a nonprovisional application of U.S. Provisional Application No. 62/305,976 entitled "Methods And Systems For Abnormality Detection In The Patterns Of Nucleic Acids," filed on Mar. 9, 2016, each of which are herein incorporated by reference in their entirety for all purposes.

BACKGROUND

The promise of artificial intelligence (AI) is just beginning to be realized, particularly in the use of machine learning (ML) models. There are many problems to be encountered and solved in various implementations of ML models. For example, the amount of variables that can potentially be used as inputs to a model can be voluminous, as can be encountered with genetic data. Training an ML model can be difficult using a large amount of input variables. And, knowing which input variables to use and how to structure the input variables is not straightforward. Further, it can be problematic when the number of samples is less than the number of features available to do inference on those samples.

Therefore, it is desirable to address these and other problems.

BRIEF SUMMARY

Embodiments provide systems, methods, and apparatuses for generating and using machine learning models using genetic data. Such a machine learning model can provide a classification of a biological sample, e.g., provide a property of the sample or subject based on measured genetic data. A set of input features for training the machine learning model can be identified and used to train the model based on training samples, e.g., for which one or more labels are known. As examples, the input features can include aligned variables (e.g., derived from DNA sequences aligned to a population level or individual reference genome) and/or non-aligned variables (e.g., sequence content). In various implementations, the variables derived from aligned reads can include one or more properties of genetic data in windows of a reference genome, and the non-aligned variables can include statistical measures of occurrence of specific data sequences in the sampled genetic information as compared to a database of genetic data or attributes.

For a training sample, the corresponding genetic data can be analyzed to obtain a training vector of the identified input features. Each element of the training vector can correspond to a feature that includes one or more variables in one or more dimensions. The training vectors can be used to train the machine learning model, e.g., by operating on the training vectors using parameters of the machine learning model to obtain output labels for the plurality of training samples. The output labels can be compared to the known labels of the training samples. Optimal values of the parameters, sampling of the features, and configuration of the features, can be iteratively searched as part of training the machine learning model based on the comparing the output labels to the known labels of the training samples. The parameters of the machine learning model and the set of features can be provided for machine learning model.

These and other embodiments of the invention are described in detail below. For example, other embodiments are directed to systems, devices, and computer readable media associated with methods described herein.

A better understanding of the nature and advantages of embodiments of the present invention may be gained with reference to the following detailed description and the accompanying drawings.

TERMS

Figure 1:
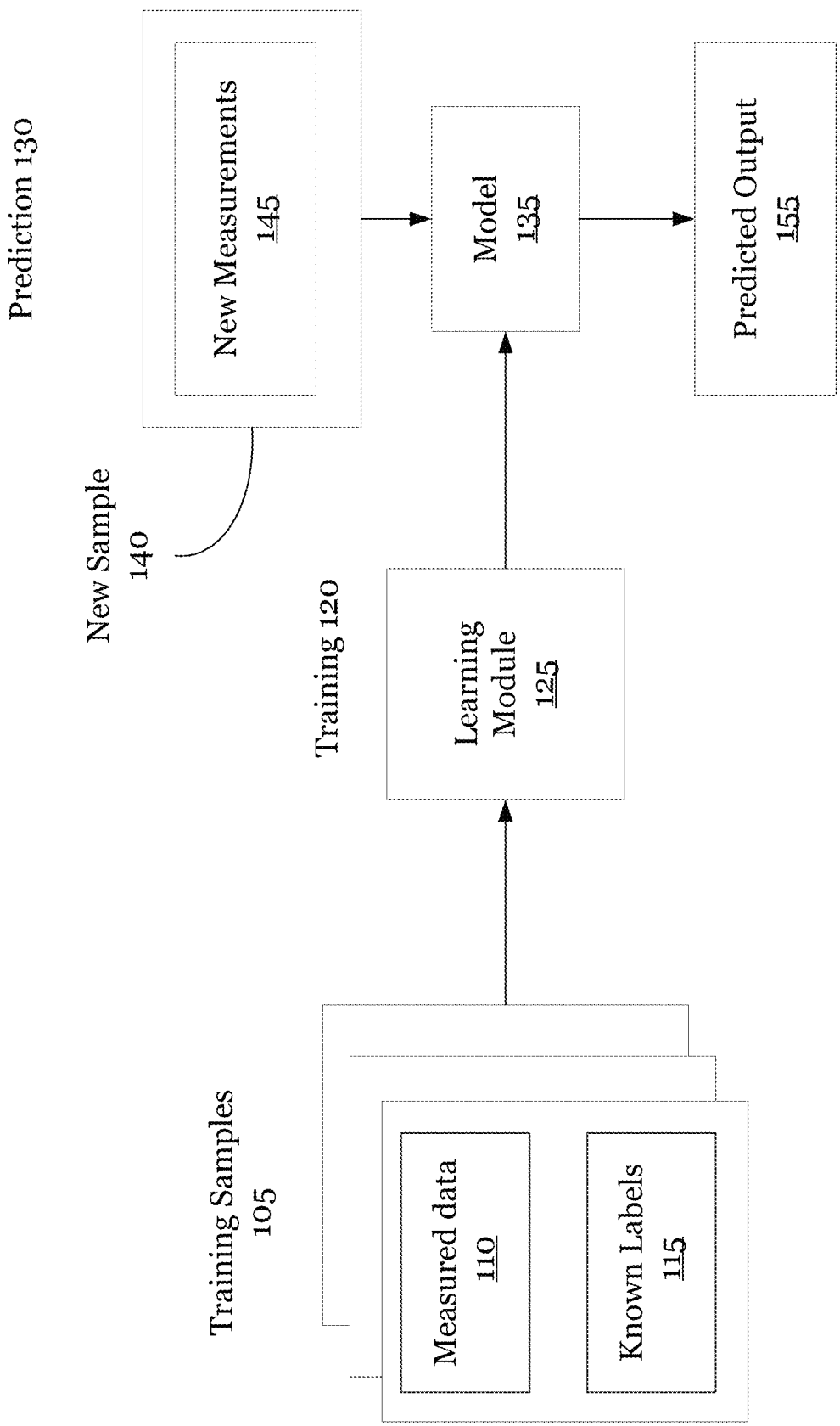
FIG. 1 shows a block diagram for usage of a machine learning model according to embodiments of the present invention

A "subject" can refer to a biological entity containing genetic materials. Examples of a biological entity include a plant, animal, or microorganism, including, e.g., bacteria, viruses, fungi, and protozoa. In some embodiments, a subject is a mammal, e.g., a human that can be male or female. Such a human can be of various ages, e.g., from 1 day to about 1 year old, about 1 year old to about 3 years old, about 3 years old to about 12 years old, about 13 years old to about 19 years old, about 20 years old to about 40 years old, about 40 years old to about 65 years old, or over 65 years old. In various embodiments, a subject can be healthy or normal, abnormal, or diagnosed or suspected of being at a risk for a disease. In various embodiments, a disease comprises a cancer, a disorder, a symptom, a syndrome, or any combination thereof.

A "biological sample" (or just sample) can refer to any substance obtained from a subject. A sample may contain or be presumed to contain nucleic acids from a subject. In some embodiments, a sample can include cells and/or cell-free material obtained in vivo, cultured in vitro, or processed in situ, as well as lineages including pedigree and phylogeny. In various embodiments, the biological sample can be tissue (e.g., solid tissue or liquid tissue), such as normal or healthy tissue from the subject. Examples of solid tissue include a primary tumor, a metastasis tumor, a polyp, or an adenoma. Examples of a liquid sample (e.g., a bodily fluid) include whole blood, buffy coat from blood (which can include lymphocytes), urine, saliva, cerebrospinal fluid, plasma, serum, ascites, sputum, sweat, tears, buccal sample, cavity rinse, or organ rinse. In some cases, the liquid is a cell-free liquid that is an essentially cell-free liquid sample or comprises cell-free nucleic acid, e.g., DNA. In some cases, cells, including circulating tumor cells, can be enriched for or isolated from the liquid.

In some embodiments, the terms "polynucleotides", "nucleotide", "nucleic acid", and "oligonucleotides" are used interchangeably. They refer to a polymeric form of nucleotides of any length, only minimally bounded at length l, either deoxyribonucleotides or ribonucleotides, or analogs thereof. In some embodiments, polynucleotides have any three-dimensional structure, and can perform any function, known or unknown. Nucleic acids can comprise RNA, DNA, e.g., genomic DNA, mitochondrial DNA, viral DNA, synthetic DNA, cDNA reverse transcribed from RNA, bacterial DNA, viral DNA, and chromatin. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, and can also be a single base of nucleotide. In some embodiments, a polynucleotide comprises modified nucleotides, such as methylated or glycosylated nucleotides and nucleotide analogs. If present, modifications to the nucleotide structure can be imparted before or after assembly of the polymer. In some embodiments, a sequence of nucleotides is interrupted by non-nucleotide components. In certain embodiments, a polynucleotide is further modified after polymerization, such as by conjugation with a labeling component.

A genetic variant (or just variant) can refer to a deviation from one or more expected values. Examples include a sequence variant or a structural variation. In various embodiments, a variant can refer to a variant already known, such as scientifically confirmed and reported in literature, a putative variant associated with a biological change, a putative variant reported in literature but not yet biologically confirmed, or a putative variant never reported in literature but inferred based on a computational analysis.

A germline variant can refer to nucleic acids inducing natural or normal variations (e.g., skin colors, hair colors, and normal weights). A somatic mutation can refer to nucleic acids inducing acquired or abnormal variations (e.g., cancers, obesity, symptoms, diseases, disorders, etc.). Germline variants are inherited, and thus correspond to an individual's genetic differences that he or she is born relative to a canonical human genome. Somatic variants are variants that occur in the zygote or later on at any point in cell division, development, and aging. In some embodiments, an analysis can distinguish between germline variants, e.g., private variants, and somatic mutations.

A structural variation (SV) can refer to a region of DNA approximately 50 bp and larger in size. Examples of SVs include inversions, translocations, and copy number variants (CNVs), e.g., insertions, deletions, and amplifications.

A machine learning model (or just model) can refer to a collection of parameters and functions, where the parameters are trained on a set of training samples. The training samples can correspond to samples having measured properties of the sample (e.g., genomic data and other subject data, such as images or health records), as well as known classifications/labels (e.g., phenotypes or treatments) for the subject. The model can learn from the training samples in a training process that optimizes the parameters (and potentially the functions) to provide an optimal quality metric (e.g., accuracy) for classifying new samples. Example parameters include weights that multiple values, e.g., in regression or neural networks. A model can include multiple submodels, which may be different layers of a model or independent models, which may have a different structural form, e.g., a combination of a neural network and a support vector machine (SVM). Examples of machine learning models include deep learning models, neural networks (e.g., deep learning neural networks), kernel-based regressions, adaptive basis regression or classification, Bayesian methods, ensemble methods, logistic regression and extensions, Gaussian processes, support vector machines (SVMs), a probabilistic model, and a probabilistic graphical model. A machine learning model can further include feature engineering (e.g., gathering of features into a data structure such as a 1, 2, or greater dimensional vector) and feature representation (e.g., processing of data structure of features into transformed features to use in training for inference of a classification).

Input features (or just features) can refer to variables that are used by the model to predict an output classification (label) of a sample, e.g., a condition, sequence content (e.g., mutations), suggested data collection operations, or suggested treatments. Values of the variables can be determined for a sample and used to determine a classification. Example of input features of genetic data include: aligned variables that relate to alignment of sequence data (e.g., sequence reads) to a genome and non-aligned variables, e.g., that relate to the sequence content of a sequence read. A training sample can refer to samples for which a classification may be known; training samples can be used to train the model. The values of the features for a sample can form an input vector, e.g., a training vector for a training sample. Each element of a training vector (or other input vector) can correspond to a feature that includes one or more variables. For example, an element of a training vector can correspond to a matrix. The value of the label of a sample can form a vector that contains strings, numbers, bytecode, or any collection of the aforementioned datatypes in any size, dimension, or combination.

DETAILED DESCRIPTION

Signals of mutations, chromosomal aberrations, structural variations, and other genomic lesions that substantiate or entail a particular phenotype often occur in relatively small amounts relative to the whole population of cells, and their mean genomic state, in individuals. It is therefore difficult to acquire enough signal intensity to detect mutations with any confidence. This genetic data can be considered sparse because of low coverage of the genome, as well as degradation of cell-free DNA. Genetic data can also be considered sparse when pairwise, or higher order, predictive relationships amongst features have spectral domain of the measured data with relatively few non-zero eigenvalues. However, such sparse measurements can still provide useful information when interactions among the measurements are taken into account.

Embodiments can generate models that take advantage of these interactions (e.g., non-linear interactions) that allow classifications of states of a sample. The measurement data can be structured in a way that the input features capture unique aspects of the biology. Further the input feature space can be searched to identify features that can provide a model that satisfies one or more specific criteria of a quality metric, such as a certain sensitivity and specificity.

Techniques of the present disclosure provide differences from published informatics approaches in previous biological studies. Each of these next generation sequencing approaches receives sequence data and outputs some kind of molecular signature or fingerprint. It is left up to a user or other software procedure to infer a biological phenotype from this molecular signature. Present techniques can design a biological machine learning (ML) system where the phenotype and the signatures/features are jointly optimized for the problem to solve.

I. Machine Learning

Machine learning is an artificial intelligence technique that allows a computer to learn from data in order to determine parameters for predicting an output of a system. In supervised learning or semi-supervised learning, a model can be trained to learn from training samples whose output classification (label) is known. The quality of a model can be highly dependent on how the input data is structured. The input data can be structured using unsupervised learning, where a model that can generate or represent the input data can be estimated. Unsupervised learning may be used in various parts of a training process.

FIG. 1 shows a block diagram for usage of a machine learning model according to embodiments of the present invention. Training samples 105 are shown to include measured data 110 and known labels 115. For ease of illustration, only three training samples are shown, but the number of training samples may be much larger, e.g., 10, 50, 100, 1,000, 10,000, 100,000, or more. Training samples 105 can include samples of different subjects, different type of sample of the same subject, and/or the same type of sample of the same subject taken at a different time.

Measured data 110 can correspond to measurements that may be readily obtained from a sample. The skilled person will appreciate the various ways that data can be measured from a sample. For example, nucleic acids in a biological sample may be sequenced to provide sequencing data. Besides such measured data, other information about a subject can be obtained, e.g., demographic information, such as age, weight, ethnicity, etc. Known labels 115 may be determined via established, but potentially time-consuming, processes, such as imaging of the subject and analysis by a trained practitioner. Example labels can include classification of a subject, e.g., discrete classification of whether a subject has cancer or not or continuous classifications providing a probability (e.g., a risk or a score) of a discrete value. The classification can have arbitrary support (e.g., a real number) or be an element of a small finite set. The classification can be ordinal, and thus the support can be provided as an integer. Accordingly, a classification can be categorical, ordinal, or real, and can relate to a single measurement or multiple measurements, and may be high dimensional.

Training samples 105 can be used by a learning module 125 to perform training 120. Learning module 125 can optimize parameters of a model 135 such that a quality metric (e.g., accuracy) of model 135 is achieved with one or more specified criteria. The accuracy may be measured by comparing known labels 115 to predicted labels. Parameters of model 135 can be iteratively varied to increase the accuracy. Determining a quality metric can be implemented for any arbitrary function including the set of all risk, loss, utility, and decision functions.

In some embodiments of training, a gradient may be determined for how varying the parameters affects a cost function, which can provide a measure of how accurate the current state of the machine learning model is. The gradient can be used in conjunction with a learning step (e.g., a measure of how much the parameters of the model should be updated for a given time step of the optimization process). The parameters (which can include weights, matrix transformations, and probability distributions) can thus be optimized to provide an optimal value of the cost function, which can be measured as being above or below a threshold (i.e., exceeds a threshold) or that the cost function does not change significantly for several time steps, as examples. In other embodiments, training can be implemented with methods that do not require a hessian or gradient calculation, such as dynamic programming or evolutionary algorithms.

A prediction stage 140 can provide a predicted output 155 for new sample 140 based on new measurements 145. The new measurements can be of a similar type as measured data 110. If new measurements are of a different type, a transformation can be performed on the data to obtain data in a similar format as measured data 110. Ideally, predicted output 155 corresponds to the true label for new sample 140.

Examples of machine learning models are provided in the Terms section above. Examples of machine learning models include deep learning models, neural networks (e.g., deep learning neural networks), kernel-based regressions, adaptive basis regression or classification, Bayesian methods, ensemble methods, logistic regression and extensions, Gaussian processes, support vector machines (SVMs), a probabilistic model, and a probabilistic graphical model. Embodiments using neural networks can employ using wide and tensorized deep architectures, convolutional layers, dropout, various neural activations, and regularization steps.

Figure 2A:
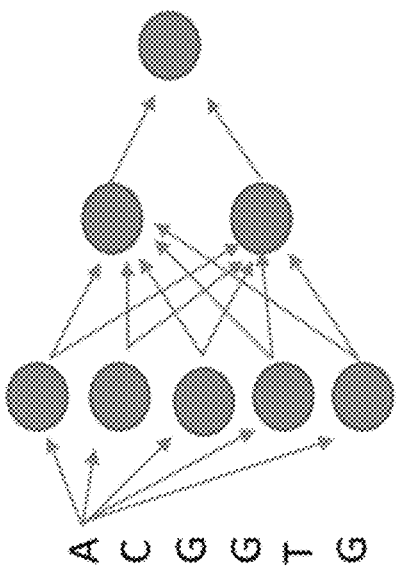
FIG. 2A shows an example machine learning model of a neural network.

FIG. 2A shows an example machine learning model of a neural network. As an example, model 135 can be a neural network that comprises a number of neurons (e.g., Adaptive basis functions) organized in layers. The training of the neural network can iteratively search for the best configuration of the parameter of the neural network for feature recognition and classification performance. Various numbers of layers and nodes may be used. A person with skills in the art can easily recognize variations in a neural network design and design of other machine learning models.

Figure 2B:
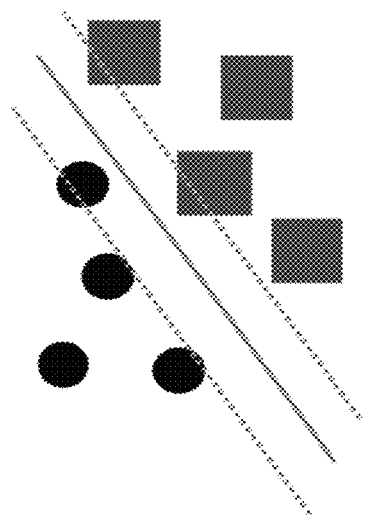
FIG. 2B shows an example machine learning model of a support vector machine (SVM).

FIG. 2B shows an example machine learning model of a support vector machine (SVM). As another example, model 135 can be a support vector machine. Features can be treated as coordinates in a coordinate space. Samples of training data points (e.g., multidimensional data points composed of the measured data). The training data points are distributed in the space, and the support vector machine can identify boundaries between the classifications.

II. Classification Problems

In the context of biology, embodiments can classify a sample as corresponding to a particular phenotype (e.g., a condition of a subject, such as a disease) or a probability of a particular phenotype. However, there are signal issues that make estimating the probability of some phenotype condition or trait measure based on measurements of genetic data (e.g., properties of molecules, such as nucleic acids). The probability of some phenotype condition may relate to mutations or chromosomal aberrations, but mutations and chromosomal aberrations often occur in relatively small amounts relative to the whole population of cells in individuals.

This is especially challenging when measuring signals from cell-free nucleic acids (cfNA). The cfDNA refers to free strands of DNA that is not located within the cell and is found in all humans, but increased in certain biological states such as after exercise and cancer. It is therefore difficult to acquire enough signal intensity to detect mutations confidently, and thus difficult to determine a classification of a phenotype condition when using simple linear combinations of the measured predictors. And, even if the amount of measured data was increased, it can still be difficult to perform an accurate inference of a phenotype condition. A reliable way to overcome these difficulties would be advantageous.

Causes of poor signals include biology, sampling procedure, technology, etc. When cfNA is analyzed, nucleic acids derived from relevant diseased cells, such as cancer cells, make up a fraction (often less than 1%) of the total cell-free population of nucleic acids. And, distinguishing between populations of measured molecules versus populations of cells can be important. In addition, the most frequently detected mutations are germline single nucleotide variations that are identified as differences against a reference genome (e.g., hg38 construct), where such variations are often a result of pedigree and not a condition.

Another cause of poor signals is insufficient depth of sequencing, which results in insufficient recovery of the biological material to derive a signal, to detect single nucleotide variants with minimal uncertainty. Since cfNA of interest (e.g. circulating tumour DNA (ctDNA), viral DNA, bacterial DNA, chromatin) often make up very a small fraction of the total nucleic acids molecules, a sample has to be sequenced to a sufficient depth in order for there to be any signal at all to detect single nucleotide variants with minimal uncertainty. A simplified example highlights the issue well. When 1% of the total population of cell-free DNA (cfDNA) comes from cancer cells and the sample is sequenced to an average depth of 100×, it is expected to see on average 1 cancer DNA molecule at any given location in the genome.

If the amount of single nucleotide mutant molecules is as low as one at a given locus in a genome, it is difficult to have a sufficient confidence level in acquired signals. This issue is compounded by the fact that known systemic sequencing error rates even on the best commercially available next-generation sequencing (NGS) systems can run at a 1-2% error rate, making it even harder to detect if a small signal is a true signal. Such signal issues cause an inability to make a diagnostic or mutational assignment decision with low uncertainty.

Complicating the issue of having poor signals is the desire to perform the analysis cheaply, and thus it is not desirable to perform sequencing at high depth. Thus, for embodiments to be used in widespread screening, it is desirable for any sequencing to have little coverage, e.g., less than 10×, 5×, 2×, 1×, 0.5×, or lower. At such low counts, it is very difficult to accurately identify specific variations with high confidence. However, embodiments can use measurements across the genome to create an input feature space that can provide an accurate classification, e.g., by accounting for a multitude of interactions among variations, covariations, and detected signals.

Another issue for machine learning model for biologics is that the number of samples is less than the number of features available to do inference on those samples. This makes biological and health machine learning a unique and different problem from other already solved AI problems.

A. Example Samples

In some embodiments, a biological sample comprises a solid biological sample, e.g., feces or tissue biopsy. A sample can comprise in vitro cell culture constituents (including, but not limited to, conditioned medium resulting from the growth of cells in cell culture medium, recombinant cells and cell components). In various embodiments, a sample may comprise a diagnosis from a cancer cell, a circulating tumor cell, a cancer stem cell, white blood cells, red blood cells, lymphocytes, and the like. In some cases, a sample comprises nucleic acids derived from about, or at least, 1%, 5%, 10%, 15%, 20%, 25%, 30%, 35%, 40%, 45%, 50%, 55%, 60%, 65%, 70%, 75%, 80%, 85%, 90%, 95%, 99%, or 100% tumor cells. A subject is suspected or known to harbor a solid tumor, or can be a subject who previously harbored a solid tumor.

In some embodiments, a sample is taken at a first time point and sequenced, and then another sample is taken at a subsequent time point and is sequenced. Thus, two samples can be collected from a subject at different times, e.g., one being at a time when the subject was healthy or had a different biological condition. One of the samples can be treated as a normal control or reference sample, from which differences of a sample can be identified. As examples, the normal sample can comprise white blood cells or normal tissue. For example, a normal subject can have regular physical examinations with his primary care physician. At each physical examination, peripheral bloods are drawn and cell-free DNA is extracted, sequenced, and analyzed based on the technologies disclosed herein.

Two samples can be collected from different subjects, e.g., where one of the subjects is considered normal and provides a normal sample. In various embodiments, one or more reference genomes can comprise one or more of the following: genomes from a normal population, a synthesized normal genome dynamically generated and personalized, a genome from a normal sample of the subject, or a genome from reference cancer tissues.

In some embodiments, a sample is obtained, e.g., from a tissue or a bodily fluid or both, from a subject. In various embodiments, the sample comprises any sample described herein, e.g., a primary tumor, metastasis tumor, buffy coat from blood (e.g., lymphocytes), cell-free DNA (cf-DNA) extracted from plasma, or bodily fluid such as urine, sputum, or mucus.

B. Example Classifications (Conditions, Treatments, Further Measurements, . . . )

Various types of signals can be processed and classifications (e.g., phenotypes or probabilities of phenotypes) inferred using a machine learning model. One type of classifications corresponds to conditions (e.g., diseases and/or stages or severity of diseases) of the subject. Thus, in some embodiment, the model can classify a subject based on the type of conditions on which the model was trained. Such conditions would correspond to the labels, or a collection of categorical variables, of the training samples. As mentioned above, these labels can be determined through more intensive measurements or of patients at later stages of a condition, which made the condition more easily identified.

Such a model created using training samples having the prescribed conditions can provide certain advantages. Advantages of the technologies include: (a) advance screening of age-associated diseases before onset of symptoms or reliable detection via alternative methods, where applications may include but not limited to cancer, diabetes, Alzheimer's disease and other diseases that may have genetic signatures, e.g., somatic genetic signatures; (b) diagnostic confirmation or supplementary evidence to existing diagnostic methods (e.g., cancer biopsy/medical imaging scans); and (c) treatment and post-treatment monitoring for prognosis report and recurrence detection.

In various embodiments, a biological condition can comprise an age-associated disease, a state in aging, a treatment effect, a drug effect, a surgical effect, a measureable trait, or a biological state after a lifestyle modification (e.g., a diet change, a smoking change, a sleeping pattern change, etc.). In some embodiments, a biological condition could be unknown, where the classification can be determined as the absence of another condition. Thus, the machine learning model can infer an unknown biological condition or interpret the unknown biological condition.

In some embodiments, there can be a gradual change of a classification, and thus there can be many levels of classification of a condition, e.g., corresponding to real numbers. Accordingly, the classification could be a probability, a risk, or a measure as to a subject having a condition or other biological state. Each of such values can correspond to a different classification.

In some embodiments, the classification can include recommendations, which may be based on a previous classification of a condition. The previous classification can be performed by a separate model that uses the same training data (although potentially different input features), or an earlier sub-model that is part of a larger model that includes various classifications, where an output classification of one model can be used as input to another model. For example, if a subject is classified as having a high risk of myocardial infarction, a model can recommend a change in lifestyle: exercise regularly, consume heathy dietary, maintain healthy weight, quit smoking, and lower LDL cholesterol.

Accordingly, embodiments can provide many different models, each one directed to a different type of classification. As another example, an initial model can determine whether the subject has cancer or not. A further model can determine whether the subject has a particular cancer or not. A further model can classify a predicted response of a subject to a particular drug or other type of treatment. As another example, a model early in a chain of sub-models can determine whether certain genetic variations are accurate or not, and then use that information to generate input feature to a later sub-model (i.e., later in a pipeline).

In some embodiments, a classification of a phenotype might be derived from a physiological process, such as changes in cell turnover due to infection or physiological stress that induces a change in the kinds and distributions of molecules an experimenter might observe in a patient's blood, plasma, urine, etc A further example for type classification is a suggestion for further measurements, which relates to a pivot diagnosis. As mentioned before, some amount of the signal problems comes from the biology itself. Computational solutions can be used to mitigate these issues to a minimal extent. For example, the model or part of the model (e.g., a sub-model) can calculate one or more variables (e.g., input features) that are lacking to determine an accurate classification. For instance, if a first measurement step was to sequence the whole genome at 3× depth and that was sufficient information to classify subject for the disease but not necessarily the nature of the disease, the model can identify further measurement steps to obtain more detail. Such a process can provide an active learning component.

Accordingly, some embodiments can include active learning, where the machine learning procedure can suggest future experiments or data to acquire based on the probability of that data reducing uncertainty in the classification. Such issues could relate to sufficient coverage of the subject genome, lack of time point resolution, insufficient patient background sequences, or other reasons. In various embodiments, the model may suggest one of many follow-up steps based on the missing variables, including one or more of the following: (i) re-sequencing whole genome sequencing (WGS), (ii) re-sequencing whole chromosome sequencing (WES), (iii) targeted sequencing of a particular region of the subject's genome, (iv) specific primer or other approaches, and (v) other wet lab approaches. The recommendation can vary among patients (e.g., due to the subject's genetic data or non-genetic data). For instance, one subject can have the route of (i)→(iii)→(iv) suggested, while another gets (ii)→

(v). In some embodiments, the analysis aims to minimize some function such as the cost, risk, or morbidity to the patient, while suggesting the best next steps to get the most accurate classification.

III. Overview of Generation of Model

As described above, embodiments can be used for a variety of purposes. For example, plasma (or other sample) can be collected from subjects symptomatic with a condition (i.e., known to have the condition) and healthy subjects. Genetic data (e.g., cfDNA) can be acquired analyzed to obtain a variety of different features, which can include features based on a genome wide analysis. These features can form a feature space that is searched, stretched, rotated, translated, and linearly or non-linearly transformed to generate an accurate machine learning model, which can differentiate between healthy subjects and subjects with the condition (e.g., identify a disease or non-disease status of a subject). Output derived from this data and model (which may include probabilities of the condition, stages (levels) of the condition, or other values), can be used to generate another model that can be used to recommend further procedures, e.g., recommend a biopsy or keep monitoring the subject condition.

Below is an overview of techniques and systems used to generate the machine learning model. Techniques are described, e.g., for measuring the genetic data, filtering the genetic data, extracting features from the genetic data (e.g., to form a feature vector), and searching the features to determine a set of features providing a model that can perform the desired classification(s) with a desired accuracy. Example systems can take assembled genomic sequences and perform probabilistic and statistical analysis to identify abnormal patterns related to a condition, as part of determining the features and the model.

Figure 3:
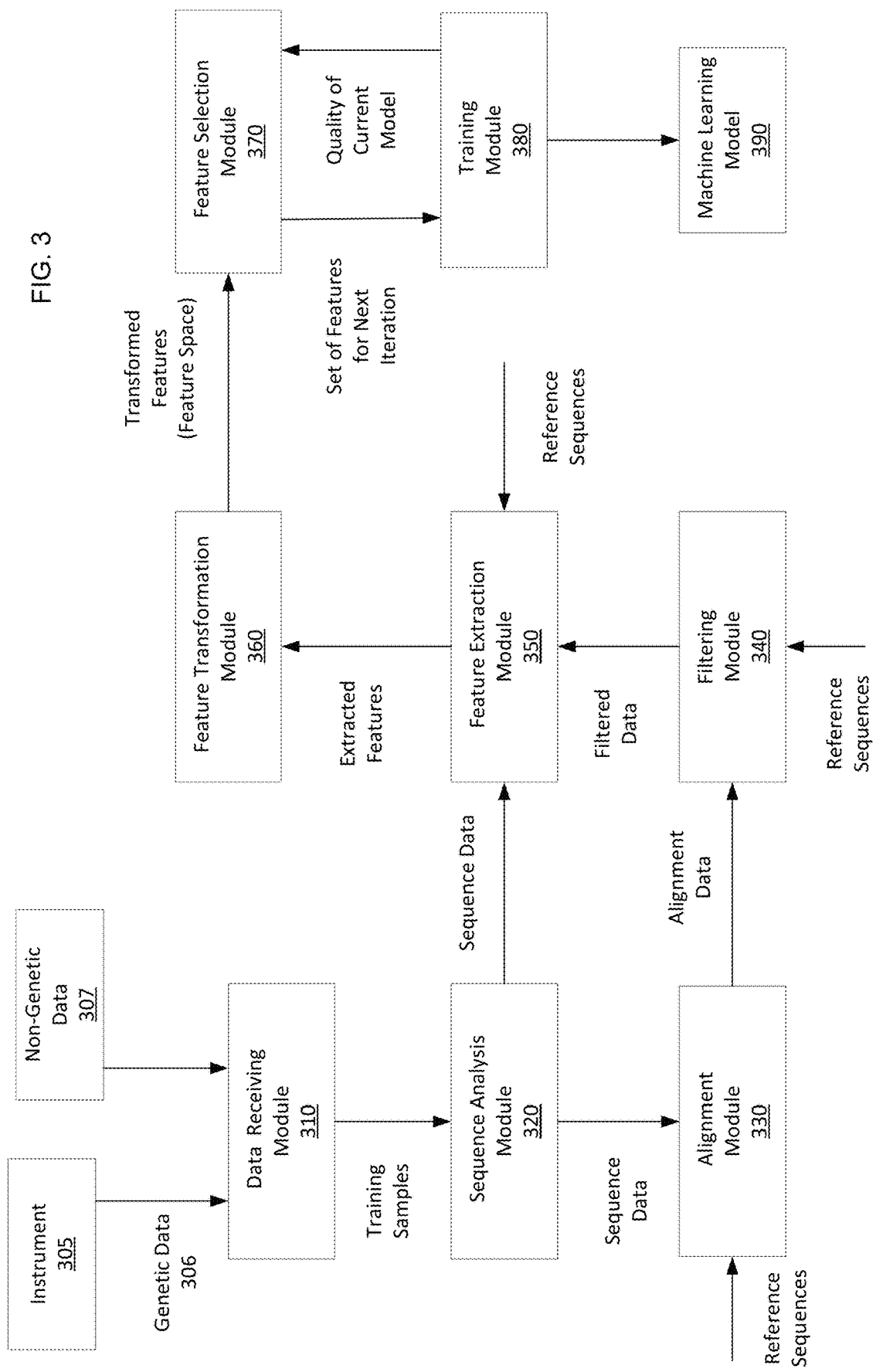
FIG. 3 shows a system 300 for generating a machine learning model using genetic data according to embodiments of the present invention.

FIG. 3 shows a system 300 for generating a machine learning model using genetic data according to embodiments of the present invention. System 300 can include various modules, but may transfer various data among themselves. Although certain communications of data are shown, other communications (not shown) of data are possible. The modules may be implemented in software and/or hardware. For example, configuration information or program code can exist for each module (e.g., stored in memory) and be used to control one or more processors to implement functions of the model. Various modules of FIG. 3 are optional, and may be performed in parallel as opposed to the sequence operation depicted. Further, various functionality can optionally be implemented in different modules.

A. Obtaining Genetic Data and Non-Genetic Data

Instrument 305 may include any physical components including hardware, software, and biochemical products, which may be used to measure genetic data 306 from a sample of a subject. Example genetic data includes sequence reads of nucleic acids, methylation information about the nucleic acids, measurements of protein bindings, and nucleosome positioning generated with ATAC-seq or MNase-seq. modifications of and extensions of the molecules aforementioned. Instrument 305 can perform one or more experimental measurements on nucleic acids obtained from a sample.

An example instrument is a sequencing instrument (e.g., a high-throughput sequencing instrument), which may sequence all or a portion (e.g., ends) of nucleic acid molecules. Example sequencing instruments include nanopore sequencing devices, machines that sequence by synthesis (e.g., using fluorescent labeled nucleotides and imaging hardware), bisulfite sequencing, pore based sequencing, other long read technologies, or any other relevant procedure. Other example instruments include PCR machines, mass spectroscopy instruments, electrophoretic machines, and nuclear magnetic resonance (NMR) machines. Any of these instruments may provide sequence reads, as they can provide information about a sequence of a nucleic acid molecule.

The biochemical products may be reagents used in the measurement process, e.g., primers or probes. Various instances of instruments or different types of instruments can be used for measuring genetic data from different samples of different subjects. In some embodiments, a lab step can comprise conducting a traditional sequencing, followed by bisulfite sequencing on the same source sample or an enzymatic treatment step. Some embodiment can enrich for particular nucleic acids (e.g., variant nucleic acids or ones of a particular region). Such enrichment can comprise one or more of the following: using a panel of primers, a hybridization-based approach, a filtration method, a size-selection method, a gel-based approach, a bead-based approach, and a pull-out method. As another example, a targeted sequencing assay may be used.

Non-genetic data 307 can include, but not limited to, age, weight, height, ethnicity, and other such physical characteristics, as well as names, dates of birth, genders, demographics, measurements of mental, physical, or physiological wellness, medical history, sample sources, sample collection times, and sample biological conditions (e.g., to be used as labels/classifications of the samples for training purposes). Such non-genetic data can provide informative biological knowledge that is used for feature representation. Non-genetic data 307 may be obtained in a variety of ways, as will be appreciated by one skilled in the art.

B. Data Receiving Module

A data receiving module 310 can be configured to receive genetic data 306 and non-genetic data 307. Data receiving module 310 can include temporary data storage, such as a memory device or a hard drive, to store the genetic data, e.g., sequence reads generated by a high-throughput sequencing instrument. Data receiving module 310 can also include a database, e.g., for storing data in particular file formats.

Data receiving module 310 can reorganize data into a predefined format and stores the reorganized data into the database. For example, genetic data of multiple subjects can be separately stored under records for individual subjects. In another example, the genetic data is reorganized based on annotated information. The genetic data and non-genetic data can be paired as part of generating the records. In some instances, when genetic data and non-genetic data cannot be paired, the data can be returned back to the temporary data storage to wait more upcoming data. As an alternative, data receiving module 310 can mark the missing data entries and store the reorganized data into the database.

Accordingly, data receiving module 310 can process the received data and send the data to later modules for analysis. For example, a sequencing analysis module 320 can analyze the sequence reads to determine collective and/or individual properties of the sequence reads.

C. Sequence Analysis Module

Sequencing analysis module 320 can analyze sequence reads of the training samples. In various embodiments, the analysis comprises read-by-read analysis or a collective analysis. Thus, the sequence analysis can be performed individually for each sample (e.g., each training sample) or collectively for two or more samples. The collective analysis can refer to the set of sequence reads within a single patient, as well as refer to the comparison of reads of a single subject to reads of other subjects.

The sequence analysis can determine a composition of Kmers in respective sequence reads, certain groups of reads, certain biological elements in respective sequence reads, certain information theoretic or probabalistic elements in respective sequence reads, or all the reads. A Kmer is a sequence of K bases. For a given K, there are $4^K$ possible Kmers. Results of the sequence analysis can be fed into a feature extraction module 350. Examples of such features are provided in a later section.

In some embodiments, sequence analysis module 320 can analyze the sequence of a read to determine whether an alignment should be done. For example, a read can be identified as belonging to a particular biological or functional category based on sequence information, such as Kmer, information content (e.g., identification of biological features, entropy, or mutual information), or some biological filter such as a collection of repeat sequence types or microsatellite types. For example, repetitive Kmers known to be biologically very unlikely to exist in a patient can be skipped. Thus, various embodiments may align all reads, only a portion of reads (e.g., according to certain criteria, such as whether a read belongs to a particular biological category), or none of the reads. In some implementations, reads from a particular category can be probabilistically filtered out of a main dataset. Other sequence labels (e.g., derived from cancer cells, healthy cells, a particular cell type, a particular cellular process, or physiological event) can also be assigned to a read based on the sequence content of the read, e.g., a germline variation or a somatic variation. Such distinctions can be considered as a biological prior on the sequenced reads being recovered and what kinds of nucleotide distributions are expected.

Such an identification of reads from particular functional categories can be used in later stages of the system. For example, a contribution of a read to a particular feature can be reduced or increased based on the properties of its sequence. Some embodiments can determine specific features for cancer-derived reads (or at least reads probabilistically estimated to be cancer-derived), as well as specific features for sequence reads not estimated to have originated from tumor cells.

Such inferring the origin and other properties of individual sequence reads can strengthen signal detected. One problem with cfNA sequencing analysis is weak signal detection. The fraction of nucleic acid fragments coming from diseased cells (such as cancer) makes up a small population of all the cells contributing to the cfNA population. Therefore, it is difficult to differentiate between genetic lesions associated with fragments from the diseased cells as opposed to normal cells.

Genetics lesions correspond to "non-normal" genetic changes measured with respects to a germline-derived reference. The sequence composition across a single read of DNA can vary between reads sequenced from normal cells and cancer cells, e.g., using a Kmer analysis. For example, a distribution over sequenced information can be derived from the sequences of both normal reads and cancer reads, and each read can be matched to the most likely generating distribution to identify read identity. As other examples, the probability of a read corresponding to a particular read category can be determined by matching the read to a particular distribution over the reference genome, over previously observed mutations, or based on the probability of the read itself given a latent generating process.

A further sequence analysis can differentiate sequencing errors from non-sequencing errors. For example, a procedure can assign or fit a distribution to the measured sequence reads. One approach could assume that the true error and sequencing error are distributed by two different multinomial/categorical distributions with their own noise components. Thus, for each base of each read (or for other measured values), embodiments can assign a probability of that particular measure, e.g., a mean plus or minus an error estimate.

Besides sequence analysis, other pre-alignment analysis can be performed to improve signal detection. The pre-alignment analysis can help in determining features related to nucleotide content, SVs, fusions, mutations, telomere attrition, and nucleosome occupancy. Sequence analysis module 320 can be optional.

Some embodiments can implement sequencing analysis module 320 as follows. Sequence reads from a sample are streamed from the sequencer to storage (e.g., cloud storage). As the reads are streamed, the set of all Kmers of specified lengths (e.g., between length k from 5 to 10) are counted in each read. A bloom filter (or other data structure) can be stored in memory and specify whether a particular Kmer has been seen at least once. Another bloom filter (or other data structure) in memory can store the count of each of those observed Kmers. After streaming and Kmer counting is complete, the bloom filter(s) can be transferred to cloud storage for possible use in generating Kmer dictionaries and Kmer count vectors for use in feature engineering procedures.

D. Alignment Module

An alignment module 330 can align sequence reads in the sequence data to references sequences (e.g., to a reference genome) or to a previously engineered Kmer dictionary. In some implementations, the alignment can be done to multiple references sequences, which may be determined from the same subject (e.g., of healthy tissue), other subjects, or theoretically generated. Instead or alternatively, a read can be aligned (mapped) to an exome. Further, sequence reads can correspond to RNA, and thus aligning can be to a transcriptome.

The alignment can be used to assemble the sequence reads into a predicted genome of the subject. As part of the alignment, a parameter sweep of various locality and mismatch parameters can be applied to the sequenced reads during alignment to identify the optimum alignment properties for the phenotype under study (e.g., condition, treatment, or other classification problem).

Some embodiments can implement alignment module 330 as follows. Sequence reads (e.g., from a FASTQ file) can be aligned to a reference genome by querying reads within a burrows wheeler transformed suffix array of the reference genome. The alignment process can associate each sequence read with an associated chromosome and location. The output of this process can be a BAM file, where each read that is sequenced is mapped to a particular location in the genome with a mapping score as well as annotation of insertion, deletion, and inversion events.

E. Filtering Module (e.g., Mutation Filtering)

A filtering module 340 can filter the genetic data based on the alignment data to provide one or more sets of filtered data. For example, filtering module 340 can estimate a first set of filtered data corresponding to germline variants and a second set of filtered data. Such sets of filtered data can be determined based on comparisons to reference sequences, or to known mutation information in DNA or RNA levels. A germline variant can be determined by comparing sequence reads of a healthy sample of the subject to a reference genome. A somatic variant can be determined by comparing sequence reads of a sample that potentially includes diseased molecules (e.g., cfNA in plasma) to sequence reads from a healthy sample of the subject, or equivalently to a combination of the germline variants and a reference genome. In determining a reference, the sequences of independent runs on different samples can be used to determine a reference. For example, if the sequences of the majority of independent runs differ from the reference, the reference sequence can be overridden.

In some embodiments, the majority of cfDNA collected from an individual, sometimes even with an advanced disease state, is not from cells of interest. Therefore, generating one set of filtered data for germline DNA and another set of filtered data for somatic DNA of the sequence data can be helpful in generating a signal to detect a target phenotype from the genetic data. Accordingly, aligned reads can be filtered based on quality metrics and informational distributions so to provide separate pools of normal, somatic-derived reads, germline-derived reads, cancer-derived reads, specific cell type derived reads, physiological event derived reads. Other sets of filtered data can relate to unknown variations or putative variations. The filtered data for germline variation DNA may ultimately be used to generate a feature vector specific to the germline DNA, where the input features can include multiple feature vectors, or a specific portion of a single feature vector. The same can be done for the filtered data corresponding to the somatic variation DNA.

In some embodiments, filtering module 340 can use reads from one biological category and not others as identified by sequencing analysis module 320 to construct genomic background of a subject. The reads used in this germline analysis can use a sample that is or presume to be nucleic acids from healthy cells (leukocyte white blood cells which, with the exception of leukemia, would be qualified as the patient background in a plasma sample). Sequencing the leukocyte DNA would minimally double the cost of analysis. By analyzing these reads aligned to a reference genome (e.g., hg38), the module can identify one or more germline variants of the subject. In some implementations, the germline variants can be removed from the analysis so that they do not contribute information when computing somatic variants, or when determining other features.

Filtering module 340 can receive various input, e.g., the alignment data, the genetic data, and references sequences. The reference sequences used as input by filtering module 340 can be the same or different than reference sequences used by alignment module 330. Reference sequences can include, but are not limited to: information from databases of published scientific documents, or information from databases of genomic annotations, or information from databases of previously analyzed samples from the same subject or from different subjects, or information from a combination of the databases thereof, a dictionary of sequences curated by previous analysis or a known biological process, or a manually engineered set of sequences.

Filtering module 340 can use sequence reads from multiple samples (e.g., of same subject at different times, different types of samples, different subjects, etc.) to provide filtered data for a current training sample. For example, filtering module 340 can identify one or more comparison metrics by comparing the sequence reads of a current training sample (e.g., a plasma sample) to sequences of a bank of sequences from one or more previously analyzed patients, the same patient, or from a database, or from a pedigree.

Accordingly, the filtering can provide information about differences between the current sample and other samples as well as information about the inter relationships between measurements within the sample itself. Thus, inter-sample and intra-sample discordance can be determined and used to obtain filtered data. In some embodiments, as part of this determination, a prediction model is constructed to predict sequences at a particular location in a genome of a sample, and differences between the prediction and actual measurements can be used to create a filtered data set. For instance, when sequences of a first sample data arrive, a prediction model can be applied to predict possible sequences in a second sample. When sequences of the second sample are measured, predicted and observed sequences regarding the second sample can be compared. In embodiments where comparison identifies discordance between prediction and measurement (observation), a potential variant can be identified for inclusion in a filtered data set, e.g., of a data set including all such discordances across the genome.

Such a prediction model can be a separate machine learning model, or considered a sub-model of a larger model. The prediction model can be trained using known variants measured from such second samples (e.g., samples at a later time), where the input features are determined from the first samples. In one embodiment, the predicted variants can be used as input features themselves, as opposed to being compared to other sequences, with the results of the comparisons used for extracting features. In some embodiments, the prediction model can estimate the origin points of mutations and model the onset or occurrence or development rates, which can be used to compute the severity of disease at a given time point and likely progression patterns. In some implementations, a variant can be scored based on the prediction model, which may be trained with sets of good (i.e., true positives) and bad (i.e., false positives) variant calls. Such scoring can be used by later modules, e.g., a feature transformation module or by a feature extraction module that incorporates a score of each of the variants into a total score that is used as a feature.

In some embodiments, filtering module 340 can take into account processing performed by downstream modules. For example, due to low coverage of mutant nucleic acids (mNAs), it is possible that at many sites, there is an insufficient number of mutant reads (MRs) to call it a mutation with statistical significance when compared against overwhelming majority of wild type reads (WTRs). Filtering module 340 can take a functional approach to overcoming this barrier. By querying the nature and downstream effect of the suggested mutation, the analysis can discern which mutant sequences as suggested by the few (n) reads are real or relevant to the disease in question.

One approach is to see if the base change suggested by the MRs is synonymous (cause protein-level sequence changes) or not. If so, these mutations are more likely to be non-functional and the synonymous mutations are filtered out. The non-synonymous mutations can then be run across a database of functional protein sequence changes. If the protein sequence in question is known to cause functional detriment, the suggested mutation can be weighted more than the ones that do not cause functional detriment. However, both cases may be kept for downstream analysis.

As another example of weighting as part of obtaining a filtered dataset, a variant (e.g., a mutation) can be assigned some positive prior probability of being mutated (e.g., it has been annotated as a mutation with phenotypic effect previously). A weight (or prior probability distribution)) of a corresponding feature can be set when inputting that index of the feature vector to model training. In this manner, such a distribution may not be strictly used in the estimation step, but used to weight the estimation because there is some information to justify setting an informative prior.

Another approach focuses on changes that occur at the RNA level. If the proposed mutation lay in areas where functional RNAs (such as tRNA, lncRNA, etc.) are coded, the analysis can perform an RNA-specific functional query. The analysis can query the proposed mutation against databases or models built of functional RNAs to see if the proposed mutation causes functional changes to the RNA in question. In some embodiments, the analysis can predict the RNA's secondary structure to see if the proposed mutation would change the secondary structure of the RNA. The mutation can be weighted based on the outcome of functional inference.

F. Feature Extraction Module

A feature extraction module 350 can extract one or more features, e.g., using the genetic data, non-genetic data, the filtered data, and reference sequences. The processing by feature extraction module 350 can be referred to as feature engineering. The extracted features can represent particular properties of the sample, and potentially the subject in general. The particular features are extracted with a goal that the some of the features have different values among different groups of subjects (e.g., different values among subjects with a condition and without the condition), thereby allowing discrimination between the different groups or inference of an extent of a property, state, or trait.

Examples of features include: a structural variation, a fusion, a mutation, telomere attrition, nucleosome occupancy, and Kmer information. A feature can be represented by a numeric number, a string, or bits. In some embodiments, a feature or a plurality of features can be represented by a matrix.

One class of features corresponds to sequence variations (e.g., mutations) in the sequence reads of a training sample relative to a reference genome, e.g., of a particular population or even from another sample. Examples of such variations (e.g., germline variations and somatic mutations) are described above. As examples, an extracted feature can relate to a number of variations in a particular region of the genome (e.g. one base position or a larger region, which may be contiguous or disjoint), a ratio of a number of variations in one region relative to another, a statistical value of number of variations across various regions, ratios of such statistical values, or results using combinations of such values. Besides specific sequence variations, sequence similarities of the reads from a training sample relative to a reference genome or reference sequences from another sample can be determined as a feature.

Another class of features corresponds to copy number variations, other types of structural variations, or simply read count. Such features can correspond to a number of reads aligned to a particular region, e.g., using all reads and not just ones with sequence variations. Using multiple classes of features can provide enhanced accuracy, e.g., enhanced sensitivity due to more signals being used As part of the analysis, feature extraction module 350 can identify comparison metrics across two input samples of a same subject. Or features can be extracted by generating comparison metrics within a single sample from a single subject. Such a comparison can be the same or similar to operations performed by filtering module 340.

The extraction process for a given feature can include multiple steps. For example, a first step can be to determine a number of sequence reads aligned to a particular region. This number of reads can be compared to a number of reads in another region, which may comprise a statistical value of the number of reads across many regions. A ratio or difference can be computed between the two numbers. Thus, an initial step can generate a first set of values, and a second step can analyze that first set of values to obtain a second set of values, and so on, until the set of features (or particular subset of the features) is determined. Different portions of the features may use different levels (e.g., number of steps) of analysis.

In some embodiments, Kernel or covariance matrices of various relational metrics over a set of reads can be calculated as a feature. For example, a longest common substring kernel over the set of reads can be applied to represent the reads in a reproducing kernel Hilbert space. Matrix decompositions such as singular value decomposition can be applied to the covariance matrices, and eigenvalue spectra for datasets can tabulated.

Such matrices can be determined as follow. A binary (or n-ary) relational metric can be calculated over the feature vector. For example, a kernel specifying some internally defined data space with a relational/metric function that preserves inner product spaces with the data space. This representation can be used to project future data as a pre-processing step for classification. Or, the representation itself can be used as a feature within the model.

G. Feature Transformation Module

A feature transformation module 360 can process the extracted features to obtain a transformed set of features, which may be used as input features for training the model. Transforming the features can improve the machine learning process. The processing of feature transformation module 360 can be referred to as feature representation. The set of transform features can be referred to as a feature space. Not all of the features in the feature space may be used in training the model, as the number of possible features may be quite large. The selection of features is provided by a feature selection module 370.

An example of a type of transformation that feature transformation module 360 can perform, weights may be applied to certain features, e.g., based on an expected importance of certain feature(s) relative to other feature(s). In some implementations, a feature can be scored by a probability of being associated with a biological change. Other examples of a transformation are a dimensional reduction (e.g., of a matrix), distribution analysis, normalization or regularization, and matrix decompositions (e.g., a kernel-based discriminant analyses and non-negative matrix factorization), which can provide a low dimensional manifold corresponding to the matrix. As further example, contractive and de-noising autoencoders can be used on a reduced-dimensioned dataset to achieve an even further efficient representation of the data for downstream learning.

Linear and non-linear combinations of a feature vector/matrix can summarize a data matrix (which in some cases are as large as a 4×3 billion), without significant loss of information and decrease in the length of the matrix to facilitate algorithm implementation. In some embodiments, the learning process utilizes auto-encoders and matrix decompositions such as non-negative matrix factorization and principal components analysis to reduce the dimensions of the genomic count matrix to a smaller size, which can enable a cheaper training of a machine learning procedure.

Transformation can help when data is sparse. Sparsity means that the signal is concentrated in relatively few dimensions with respects to the dimension of the manifold of the sample data. For example, the reads aligned to a genome may only cover certain part of the genome. This can mean that the data obtained from the sequencer can be used to estimate a biological phenotype with relatively few measured values or that the transformations used to estimate the phenotype given the data can concentrate the information processing in few total operations. But, the number of total features may be large, thereby obscuring the strong signal in a few features. Sparse algorithms can reduce the number of features, and thus provide good performance when the number of features is large. Sparse algorithms correspond to a class of methods that seek to find relatively fewer total transformations to move from input data to output. That output can include a classification, but could also include some intermediate data transform step.

In further examples, to assess feature representations and classification integrity prior to and in tandem with deep learning various other supervised learning methods can be employed. For example, support vector machines can be used to tune hyper parameters and get benchmarks points for feature engineering including, but not limited to, kernel selection for the specific feature. Gaussian processes are used in the feature space to derive covariance metrics with good downstream classification properties. Accordingly, machine learning can be used to determine a training procedure or priors to start the training process and for joint feature space/training space exploration.

Another example transformation can transform features determined from one type of instrument to another type of instrument. The machine learning models can be agnostic to the specific experiment being conducted. Thus, for example, if the system was switched from one type of sequencing to mass spectrometry, a matrix transformation can operate on the feature vector determined from the mass spectrometry to provide the feature vector in a proper format. The values of the matrix transformation can be learned, e.g., in a training process.

A covariance matrix can be calculated between the sample distributions of biological counts for a particular feature class (e.g., read counts 420 from FIG. 4) or a sample class (e.g., all samples having a same known phenotype label). The biological count distributions and vectors for a particular patient phenotype or feature class can be obtained. The covariance matrix can be calculated using the vectors and the mean of the count distribution. This covariance matrix can be stored as a property of a particular phenotype.

Such a covariance matrix can encode the pairwise direction of variation and magnitude of variation between each feature for a particular class of features or samples. The covariance matrix for a particular class permits information to be shared between features and enables the co-weighting of particular feature elements within downstream analysis. This is especially useful when the data recovery is sparse when trying to estimate and define a signal for predicting a phenotype because only partial information needs to be recovered because the covariation matrix can be used to re-weight biological count features by their expected mutual co-occurrence and covariation.

H. Feature Selection Module

Feature selection module 370 can select a set of features to be used in a current iteration of training the machine learning model.

Which features to extract can be informed by output data from other modules. In some embodiments, a learning process calculates features across the entire genome of a given sample. Certain features may work well in combination with other features. In some embodiments, an input feature to a machine learning procedure can be the amount of variant, mutated, or lesioned sequences seen at known cancer hotspots to inform likelihood of mutations in those hotspots as well as the rest of the genome, dictated by factors such as proximity to hotspot regions both along the DNA molecule and 3D distance (as calculated from Hi-C sequencing data, or any other sequencing method that obtains relational measures in trans or cis genomic space) as well as number of "mutated" reads seen in those specific regions in prior time points.

I. Training Module

A training module 380 can use the selected features to train the current version of the machine learning model. Values of the selected features free to the training samples can be used in conjunction with the known labels (e.g., conditions) of subjects corresponding to the training samples, in order to optimize parameters of the model to provide accurate classifications. Ideally, the classifications of a training sample (or a validation sample) should correspond to the known labels. Such accuracy can be provided as a percentage accuracy.

Accordingly, the learning (training) process uses these selected features for specific phenotypic classifications, e.g., to assign a probability of a phenotype. The various features (e.g., combinations of copy number variations at particular regions or sequence variations at particular locations) can be identified as corresponding to a particular condition, e.g., provided a sufficient number and variety of training samples are used and provided the set of selected features include features that are predictive of the condition.

If the training does not provide sufficient accuracy (e.g., after a certain number of optimization steps or after a certain amount of time), then control can return back to feature selection module 370. A new set of features can be selected. The new set of features can change in various ways relative to previous set(s) of features. For example, the new set of features can simply add additional features. In another example, certain features can be omitted and others included. Further, certain features can be concatenated together to form a new feature, and those previous features can be retained individually or dropped. For instance, the accuracy of the model for a given set of features can be 60% sensitivity and 60% specificity, which would likely be below a desired accuracy. The system can then look back for another iteration by selecting another set of features. A new training process would then use the new set of features to optimize parameters for new version of the model. If the accuracy is sufficient for the new set of features, then the trained model can be output by providing the optimize parameters and the set of features.

Figure 4:
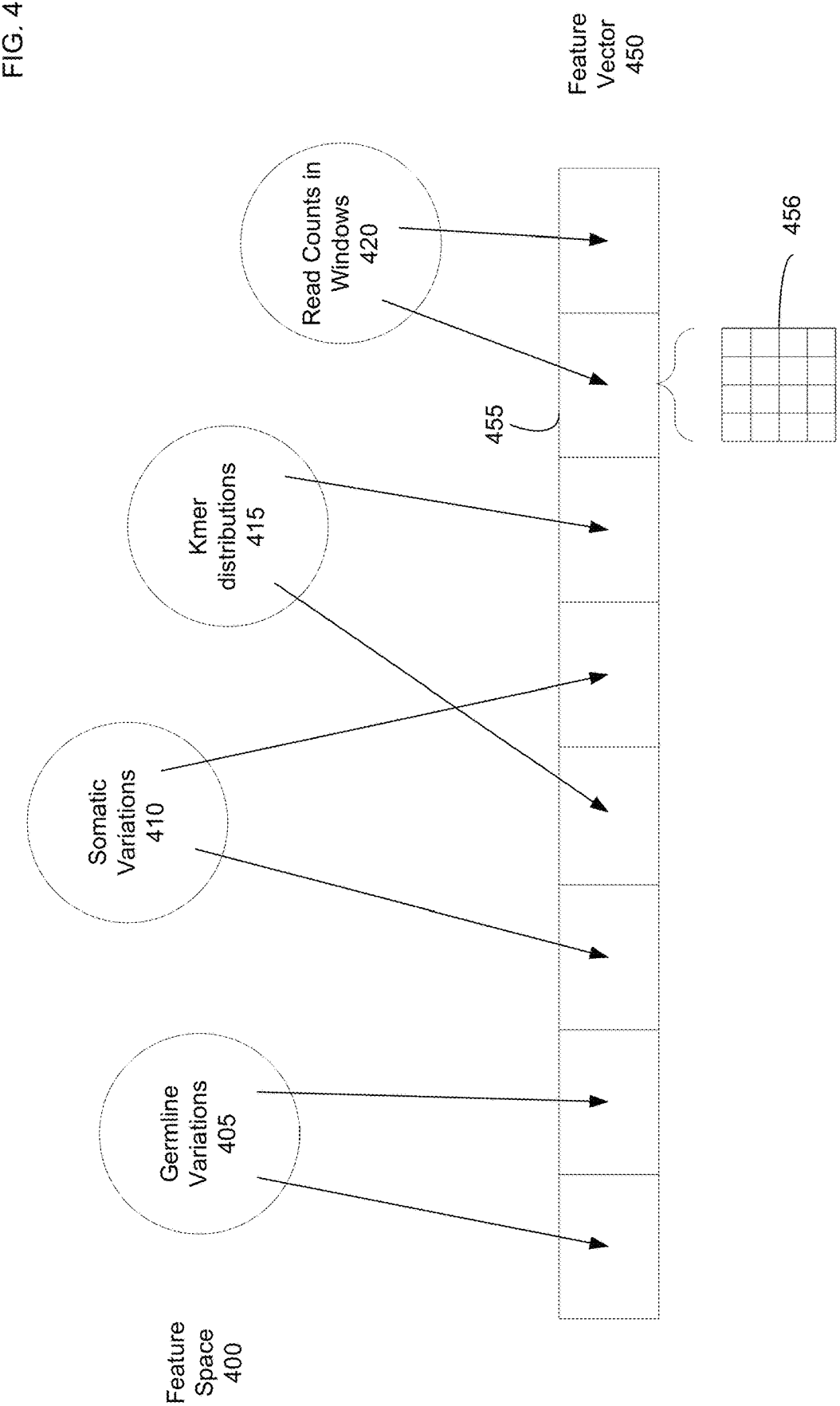
FIG. 4 shows a diagram illustrating a feature selection process according to embodiments of the present invention.

FIG. 4 shows a diagram illustrating a feature selection process according to embodiments of the present invention. Feature space 400 is shown to include extracted features corresponding to various feature classes, such as germline variations 405, somatic variations 410, Kmer distributions 415, and read counts 420 (e.g., a count of a number of reads aligned to each of a plurality of windows). Other feature classes can exist, e.g., as described herein. Each of these classes can contain many different features.

FIG. 4 shows features from various classes being selected and added to a feature vector 450, which can be used in a given iteration of training of a model. Feature vector 450 is shown having 8 elements, but can include more or less elements. Each element can correspond to a single value or a collection of values, e.g., be an array such as a matrix. For instance, element 455 can correspond to a matrix 456. The rows in the matrix can correspond to different chromosomes, and the columns can correspond to read counts within windows (or sets of windows when the count is a sum across a certain set of windows) of the chromosomes. The windows can be the same across the chromosomes or be different.

Once defined, feature vector 450 can be determined for each training sample. This set of feature vectors can then be used to train the model. For a given model, a known classification can be assigned to each feature vector for use in training the model (e.g., by comparing a predicted classification to the known classification).

The determination of accuracy can be based on the training samples and/or a separate set of samples (validation samples). In one example, a measure used for evaluating performance is based on a receiver-operating-characteristic (ROC) curve. Ideally, the curve is a step function leading to 100% accuracy. Different algorithm designs and the number of features may lead to various results for a desired performance.

J. Model

Once trained to have the desired accuracy, machine leaning model 390 can be used to classify new samples. Such operation can be called a production run. Certain modules can be used in the production run to determine the values of the set of features used in the successful training of machine learning model 390. Any of the modules used in determining values for features can be used. For example, sequence analysis module 320, alignment module 330, feature extraction module 350, and feature transformation module 360 can be used in a production run.

In various embodiments, machine learning model can comprise deep learning, neural networks, or adaptive basis regression (e.g., using splines) for classification. In certain implementations, the model can begin with a core of multi-layer perceptrons for deep learning of count and Kmer dictionary data. Each layer can filter out features that are less relevant for classification while preserving and combining the signal in ways useful for the classification problem. In some applications, stochastic gradient descent is applied to sequence and graph embedded network architectures for the classification of the labeled genomic data. In some embodiments, a model can include regression for non-binary classification problems (such as age and severity).

In some embodiments, the machine learning model is a support vector machine (SVM) based supervised learning model implemented with a kernel that can assign distance measures between sequence reads where mutated sequences preserved across multiple time-point across multiple patient samples are more likely to be causative. In further embodiments, the model can expect true mutations to be clustered, and the vector machine is geared towards detecting and learning relevant mutations by calculating discordance of clusters of mutations across multiple time points. This analysis can aim to "learn" the conserved mutation pattern during disease development rather than the nature of the specific mutations themselves although they may filter into the final decision.

Non-genetic data can be useful for training the machine learning model. For example, by constructing a machine learning model (e.g., regression model) among datasets of different age groups, the learning process can determine the extent of genomic alterations (SVs, fusions, etc.) that are associated with a given age. This allows proper normalization against the age of subjects, as well as enabling detection of genomic signatures that are "abnormal" for the age, location, or demographic regardless of whether the system has learned the specific genomic markers for a certain disease or not. This understanding of "normal" extent of genomic alterations for a specific age, location or demographic group enables a system to calculate the expectation of molecular health of a subject which represents how healthy the subject's DNA is compared to the average of the same age, location, or demographic group.

Some embodiments can comprise visualization techniques. A learning process can consider various ways to normalize cfNA datasets coming from different subjects (based on age, etc.) such that when a system visualizes processed data, a user can easily tell at a glance the extent of damage across the genome. This normalization can be enabled by regression of genomic data onto, for example, age and understanding the molecular properties of a contextually defined "normal."

In some embodiments, machine learning model 390 can output probabilities of being in different classifications, and a classifier node (or other output layer) can classify based on the probabilities. Such an output layer can be considered as part of machine learning model, even if certain parameter are selected manually or by other heuristics outside of a training process.

Various modules (e.g., besides training module 380) may implement their own machine learning techniques, e.g., sequence analysis module 320 can classify sequence reads and filtering module 340 and filter data (e.g., variants) into separate datasets.

IV. Examples Input Features

Various features of genetic data can be used in embodiments for generating machine learning models. The determination of features can include feature engineering (e.g., gathering of features into a data structure such as a 1, 2 or greater dimensional vector) and feature representation (e.g., processing of data structure of features into transformed features to use in training for inference of a classification). As examples, the features can be transformed to complex or real data types, as well as integer data fields.

Examples of features can include variables related to structural variations (SVs), such as a copy number variation and translocations; fusions; mutations (e.g., SNPs or other single nucleotide variations (SNVs), or slightly larger sequence variations); telomere attrition; and nucleosome occupancy and distribution. These features can be calculated genomewide. Example classes (types) of features are provided below.

A. Aligned Features

In some embodiments, identifying the one or more variants comprises a comparison with one or more reference genomes. In some embodiments, the one or more reference genomes comprise one or more of the following: genomes from a normal population, a synthesized normal genome dynamically generated and personalized, and a genome from a normal sample of the subject. Such aligned features are described in more detail below, e.g., with regard to sequence variants relative to another genome and with regard to counts of sequence reads, as may occur with copy number variations. The aligned features may be determined within one window (a contiguous region) or within several windows (disjoint regions).

1. Sequence Variations

A sequence variation can be identified based on differences (discordances) of the sequence read and a reference sequence at the location of alignment (mapping). A sequence read can be mapped to a location in a reference genome, but there can be mismatches. For example, a sequence read can have an A at a particular position, but the reference genome can have a G, resulting in a SNP. As mentioned above, such a SNP or other variation can be identified as a germline variant or a somatic mutation. Different variations and different types of variations (e.g., germline or somatic) can be tracked for each read. Thus, features can be generated for each variation (e.g., numbers of SNPs, numbers of inversions, total length of inversion, etc.), as well as distributions of variations across type (e.g., numbers of different variations identified as somatic).

Accordingly, such features can be for specific sequence variations existing (or a number of reads exhibiting a variation at a particular location) or aggregate values across different variations. Values at a particular location can include a potential depth of mutational "signal" reads by calculating the fraction of reads (e.g., <10%) that show a different base (or insertion or deletion) than the majority of the reads (e.g., >90%).

Alignment of a read (DNA or RNA) can also be to other genetic sequences besides a genome, e.g., an exome or a transcriptome. Thus, identifying a sequence variant can comprise identifying a difference between an RNA molecule and a reference sequence, such as a change in a RNA coding region. Such another type or class of variation can also be tracked, such that one or features specific to an RNA variation or an exome variation can be tracked. Certain variations can be counted in multiple classes, and thus a single variation can contribute to multiple features.

Differences in a protein molecule relative to a proteome can also be identified and used in generating features. For example, a non-synonymous protein sequence change can be identified.

Different classes of variations can be determined in different ways and at different modules in the system. In some embodiments, to successfully generate a genetic germline feature vector is based on sequencing the patient-matched background genomic information such as the DNA of leukocyte white blood cells which (with the exception of leukemia) would be qualified as the patient background.

In some embodiments, a variation at a particular location can be a predicted variation, which can be dependent on sequence reads at other locations. Such a prediction model is described above in relation to filtering module 340.

2. Windows

Certain features relate to properties within a set of one or more windows. For example, a count of a number of reads aligning to a window of a reference genome can be included in a feature. As described in FIG. 4, such reads counts can form a matrix, which can be an element in a feature vector of each training sample that is used to train the model.

In various embodiments, a window can comprise at least 1 base pair, at least 2 base pairs, or at least 100 base pairs, or at least 500 base pairs, or at least 1000 base pairs, or at least 2000 base pairs, or at least 3000 base pairs, or at least 4000 base pairs, or at least 5000 base pairs. The placement and width of the windows can be dynamic, e.g., to address structural variants (SVs), such as insertions, deletions, and translocations. In some embodiments, a window can be an entire chromosome. For example, a cfDNA analysis for non-invasive prenatal testing (NIPT) can take entire chromosomes, such as chromosome 21.

In embodiments where specific diseases (e.g., cancer) are considered, the window size of interest can be smaller than that of an entire chromosome and largely varied. For example, an analysis can generate a window size to be between 100 bp and 5000 bp. The windows can be sliding (i.e., overlapping) or non-overlapping.

3. Counts in Windows

Once windows are defined and locations of reads are determined, read counts can be determined in the windows. Multiple read counts can be determined for each window. As examples for one window, one read count can correspond to reads having a germline variant within the window; another read count can correspond to reads having a somatic variant within the window, and yet another read count can correspond to all reads within the window. The number of structural variants, such as insertions, deletions, and inversions can also be counted for each window. Thus, read counts can be for all reads or just certain reads having certain properties, which may include particular sequence content.

Such read counts can relate to copy number variations or any other structural variation. For example, a window having an amplification would have higher read counts than a window not having an amplification. But, when the sequencing coverage is low (e.g., less than 1×), copy number variations may lose their meaning. Even in such situations, patterns of read counts have still been useful in classifying a condition, e.g., cancer.

Accordingly, in some embodiments, a sliding fixed window or a variable length window of known genomic elements can be used to map and query those aligned sequence reads to the particular genomic window that the read most likely belongs to. The counts queried can be summarized within a vector where each index of the vector corresponds to a particular fixed sliding or variable length window. In some embodiments, if a read maps to two different windows then a fusion is counted corresponding to both of those mapped windows. A fusion can be a feature category. A fusion is defined by one section of a read mapping to one location of the genome and another section of a read mapping to a different section of the genome.

In various embodiments, pairwise and/or ensemble metrics may be determined from the reads mapping to particular windows. For example, a ratio of counts for two different windows can be determined as a pairwise metric. A ratio between a read count for chromosome 21 can be compared to that of chromosome 9 (or to the whole genome) to see if there is aneuploidy of chromosome 21.

Examples of ensemble metrics include average read counts or set of windows, or a median, mode the moments, or some other property, of a distribution of read counts. Another ensemble metric can be minimum or maximum values for a window. For example, a fraction of reads showing a variation relative to a reference or relative to other reads in the sample can be computed at each positon within a window, and an average can be computed for the window. A minimum or maximum of such can average can be determined. Any averages can be weighted averages, where the weighting (e.g., normalization) can be by length of a window or by a number reads aligned to a window. In some implementations, the greater the number of reads covering a window, the more weight is given to a value calculated within that window to the overall average. In some cases, this assumes that areas of the genome covered by more reads give a more accurate fraction than the areas with less coverage.

Another implementation can perform a comparison (e.g., a measure of distance or of a metric) between the measures determined previously in read count windows. For example, the pairwise distance between the distribution of reads calculated over windows is calculated using the maximum mean discrepancy (MMD) between distributions. Within sample read topology distributions that were calculated over genomic bins (windows) of fixed or variable length over the genome are downloaded for a particularly sample. Between each window the MMD, a measure of distance between distributions that takes into account shape and magnitude can be used to assess the distance between each window's distribution of reads (i.e., the read counts in the windows). This collection of pairwise bin shape distances can be used to encapsulate the complexity and heterogeneity of genome wide read binning within the defined windows.

4. Other Measures in Windows

Measures other than read counts can be determined from reads mapping to a particular window, and the counts of reads mapping to a particular window can vary and can include numerous biological elements. For example, the ratio of mapped guanine and cytosine nucleotides to mapped adenine or thymine nucleotides can be counted for a window. Further properties can be determined for each window. For example, the entropy of each read in a window is counted, which can provide an entropy measure of the window. The spatial distribution of reads along a reference in each window can also be calculated. The spatial distribution can correspond to the spatially defined density of reads within the window or the relationship amongst read ends within the specified window. Such read count value(s) and entropy (as well as other measures) for a window can be concatenated for use as a single feature vector, thereby allowing all of the values of a window to be treated as a single feature. Such different values can also be used as separate features, e.g., since each of the elements of a feature vector are defined in the same manner across training samples.

Another measure can include a smoothing of a particular set of values for the windows. For instance, a moving average can be determined, e.g., by taking an average over a current window and its neighbors. In one implementation, a normalization can be done to mitigate biases in a particular window.

Another measure can be a sequence similarity of reads aligning to a window and a reference sequence for the window. The sequence similarity can be measured in various ways. For example, a number of bases of reads differing from a reference can be counted. Such a measure can provide a distance of the sequence reads from the reference genome or a reference dictionary in that window. The similarity can be determined for various references, e.g., different references for different populations.

Similar measures that can be determined genomewide can also be determined for each window. For example, nucleosome occupancy, telomere attrition, and fusions can be determined.

5. Example Feature Generation

Figure 5:
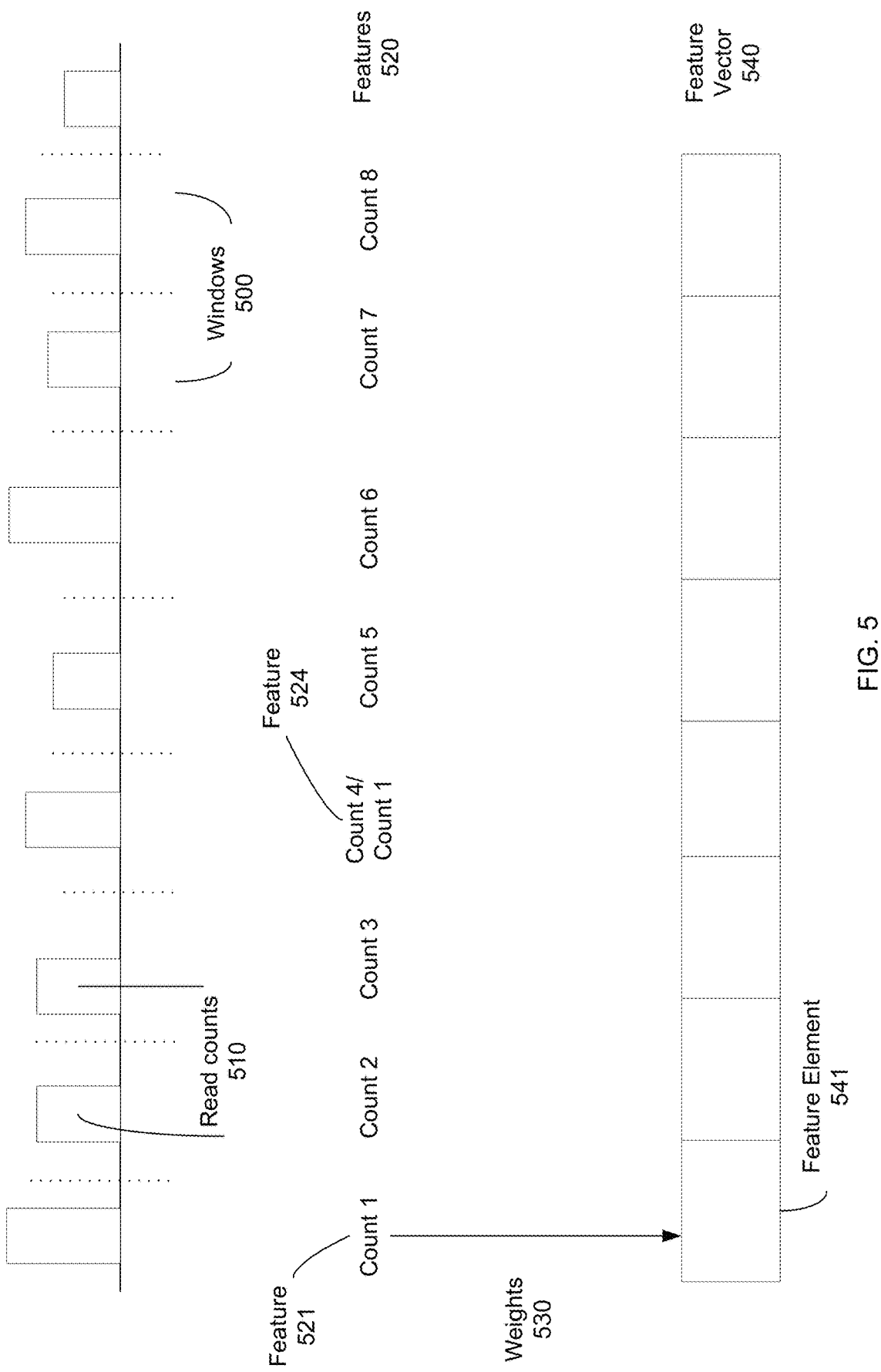
FIG. 5 illustrates usage of read counts within windows for generating a feature vector according to embodiments of the present invention.

FIG. 5 illustrates usage of read counts within windows for generating a feature vector according to embodiments of the present invention. FIG. 5 shows windows 500 as different regions across a genome (e.g., across a same or different chromosomes). The bars indicate read counts 510. The heights of the read counts are meant to convey different numbers of reads that map to each window. This example shows a different feature being determined for each window. However, more than one feature can be determined for a window, and potentially a single feature can be determined from read counts in multiple windows.

Features 520 show values for each window, labeled as Count 1, Count 2, etc. . . . . . Feature 521 corresponds to a read count for first window. To illustrate other possibilities, feature 524 corresponds to a ratio of a read count for a fourth window and the read count for the first window. Before being used to generate a feature vector 540, weights 530 may be applied to features 520. As shown, feature 521 (Count 1) is used for feature element 541. A particular weight can multiply Count 1, e.g., to emphasize or deemphasize the feature relative to other features. Such weights can allow knowledge of certain biology to inform the machine learning process. For instance, a particular window may correspond to a particular functional site that is deemed to have high importance due to its functionality.

Although feature 524 is the only feature shown as being a ratio, such a ratio can be computed for any of the windows. And, more than one feature can be determined for each window. Thus, a pure read count and ratio of read counts can both be determined for a window.

Figure 6:
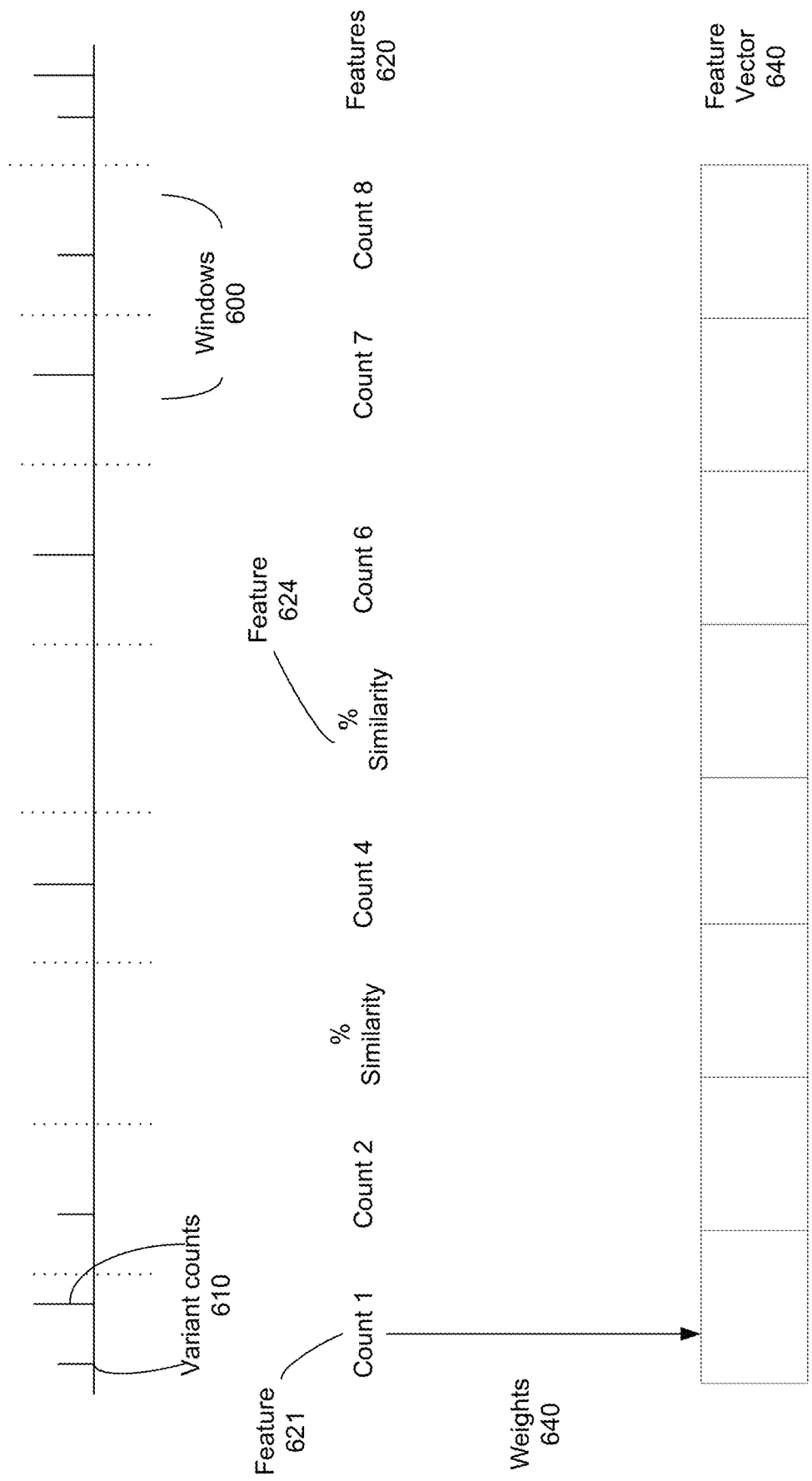
FIG. 6 illustrates usage of variant counts and sequence similarity within windows for generating a feature vector according to embodiments of the present invention.

FIG. 6 illustrates usage of variant counts and sequence similarity within windows for generating a feature vector according to embodiments of the present invention. FIG. 6 shows windows 600 as different regions across a genome (e.g., across a same or different chromosomes). The vertical lines indicate variant counts 610 at locations within the windows. Windows can have one or more locations in which a variant has been identified. The heights of the variant counts are meant to convey different numbers of reads with the variant at the locations.

Features 620 show values for each window, e.g., labeled as Count 1, Count 2, % similarity etc. Feature 621 corresponds to a variant count for first window. The variant count can be a total of both individual variant counts 610 within a first window. As another example, Count 1 can be just the variant count for one of the locations at which a variant is identified. To illustrate other possibilities, feature 624 corresponds to a read sequence similarity measure. Before being used to generate a feature vector 640, weights 630 may be applied to features 620, as in FIG. 5.

B. Non-Aligned Features

Knowledge of where a sequence read aligns may not be necessary to generate an accurate model. Further, when the genetic data is extremely sparse, the alignment data may not provide significant discriminative power. Non-aligned features can provide sufficient data without the extra step of alignment, or may add additional, different features needed to achieve higher accuracy for the model.

There are various types of non-aligned features, e.g., sequence content of a read, length of a read, biologically-derived information from reads, a change in a protein level, and a particular secondary structure of a nucleic (e.g., RNA or DNA). As examples, the sequence content can be defined based on a sequence complexity (e.g., percentage of different bases seen in the read) or based on a Kmer count. Kmers refer to a certain sequence of the DNA character strings of length K. As alignment is not performed, any type of nucleic acids can be measured, e.g., mitochondrial DNA, viral DNA, and bacterial DNA.

1. Kmers and Kmer Database

Nucleotide and information-based measurements summarize more abstract genomic features and are represented as sequence level features, such as Kmers and genome wide features, such as information content distribution along a reference. Since vast amounts of the genome is repetitive (especially for a small K), defining a set of Kmer sequences and then tabulating how frequently they appear in a region of the read sequence allows for a comparison of sequence properties within that region. This enables the ability to capture changes in sequence composition that might be exemplified by fusions, telomere length, and microsatellite instability. It can also limit the feature input space of 3 billion bases down to a small set of Kmer histograms, vectors, or graphs.

A Kmer database can store the Kmers that are to be used in the analysis (e.g., all Kmers within a specific range of lengths, such as 4-8 bases). For a given sequence read, a Kmer might exist several times or not at all, depending on the length of the Kmer. Longer Kmers will be less likely to appear. A Kmer can be identified in a sequence read by taking a first consecutive string of K bases, and incrementing a counter corresponding to the string. Then, the set of bases can be slid forward by one position to obtain the sequence from position 2 to K+1. A corresponding counter can be incremented for this Kmer as well.

Each sequence read can have its own set of counters, which can form a histogram. Such a histogram can be referred to as a Kmer dictionary. Thus, a Kmer dictionary can include all the Kmers that were seen in a read, along with the number of times each Kmer was seen in the read.

2. Example Statistical Values Using Kmers

Various features can be generated based on the Kmer content of the reads. A Kmer analysis can be used for filtering reads individually (e.g., determining what later steps are done or assigning a weight/score to the read), but for feature generation a Kmer analysis may be most useful when used to determine information collectively about the reads of a sample. Thus, some features can provide information about the Kmer content across the reads of a sample or the relation of the content of the reads to each other.

One example use of Kmers is to calculate a covariance matrix, also known as a kernel, which acts as a measure that relates the reads to each other. Instead of a single value from each read, a covariance matrix or values representing global properties of the matrix can provide quantities amongst all the reads. A Kmer distribution can provide the counts of every possible Kmer within a specific range of K that occur on a set of one or more reads. The Kmer distributions provide information about which Kmers are more represented on a read.

To determine the covariance matrix among reads, a Kmer distribution can be determined per read amongst all of the reads in a single sample. Such a distribution (histogram) can have many thousands of members. The pairwise relationship between the moments or density of that distribution and the moments or density of Kmer distributions on every other read provides a matrix for a single sample. The rows and columns of the matrix would be all of the reads. Each matrix element would provide a relation between the Kmer distribution on one sequence read relative to the Kmer distribution on another read. This can be determined as an integral over the convolution or relative entropy between distributions, or more simply a sum of a multiple of each corresponding count in one histogram times the count in the other histogram.

Figure 7A:
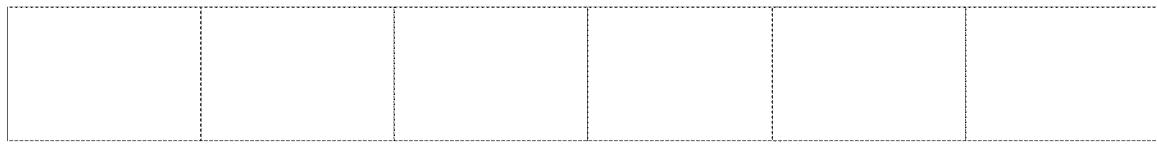
FIG. 7A shows an example Kmer histogram according to embodiments of the present invention.

FIG. 7A shows an example Kmer histogram according to embodiments of the present invention. In some embodiments, the data structure can include a number of instances a particular Kmer is encountered on a particular read, or on a set of reads. In other embodiments, the data structure can include the number of reads that a Kmer is encountered.

Figure 7B:
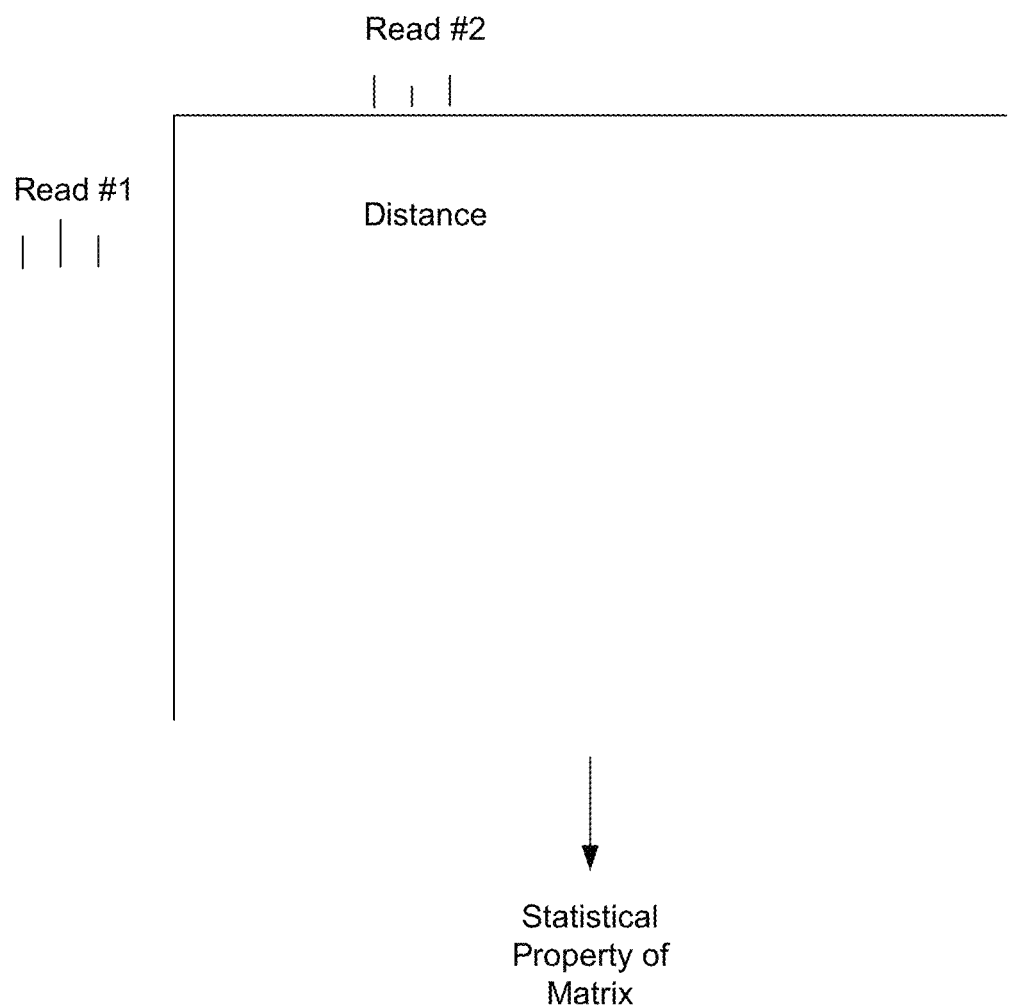
FIG. 7B shows an example covariance matrix among sequence reads of a sample according to embodiments of the present invention.

FIG. 7B shows an example covariance matrix among sequence reads of a sample according to embodiments of the present invention. A first Kmer histogram is shown for Read #1, and a second Kmer histogram is shown for Read #2. The histograms are depicted with lines of different amounts, relating to amounts of different Kmers. A distance can be computed for each matrix element based on a distance between the two Kmer histograms (distributions). Such a distance can be a difference in the number of times a Kmer is present in the two histograms. A sum of the differences can then be determined.

An example of how Kmer content can indicate a biological class of a read is as follows. Within numerous processes of aging, development, as well as genetic disorders microsatellite instability can result in the generation of trinucleotide repeats, which is the observed increase frequency of specific triplets of nucleotides in the DNA sequence that are not presented within the reference. These events can be detected and counted with read sequencing and Kmer analysis. For example, a Kmer histogram of such a read can have a large spike for one particular Kmer that is the subject of the repeat.

3. Biologically Derived Information from Reads

Unaligned reads can be mapped to vectors in biological count dictionaries where each key in the dictionary is a named category of some biological function as opposed to a name of a discrete genomic element in sequence space, such as a particular gene, open reading frame, repeat element, etc., which is defined by its chromosomal location. As examples, a category can include transcription factor binding sites, or particular kinds of trinucleotide repeats or microsatellite expansion. An example of biologically-derived information from reads includes protein binding and interaction sites. For example, numerous proteins other than transcription factors can bind to specific motifs within the genome. The frequency of these motifs for specific proteins of interest can be calculated, such as genomic patterns/motifs where HLA, CTCF, or other chromatin associated proteins are frequently observed.

A sequence analysis of reads (e.g., by sequence analysis module 320) can identify certain genetic properties of the sequence read based on the sequence content alone, without needing to align to a reference genome. For example, transcription sites can be identified based on encountering a particular sequence in the read. The particular sequences corresponding to such sites can be determined, and entered into a database such that their existence can be identified. For example, the number of transcription factor binding motifs on a read can be counted.

A collection of all transcription factor binding sites (TFBS) can be maintained and updated according to online databases such as JASPAR. Functional connections to these binding sites, such as, genes that are targets of the output of the binding sites activations can also be collected from online databases such as STRING-db. The collection of TFBS can be used as keys for a dictionary of counts for each sample. Each key of the TFBS dictionary can be used to probabilistically query each read of a particular sample. If a TFBS is identified within a read, that TFBS key can be increased in value by one. Further, each target of the gene that that TFBS activates, the key is increased in value by one in a dictionary of gene targets generated from the above database. Each dictionary can be stored on memory while being counted. However, once every read has been queried within a particular patient's FASTQ, the data structure can be stored in cloud storage to later be converted into a feature vector for further processing.

Sample distributions of biological counts belonging to particular categories including repeat element families (ALU, LINEs/SINEs) or microsatellite types can be generated from vector representations of biological count dictionaries. The biological count dictionary can be stored as a vector of counts. The sample distribution of those counts can be calculated and stored as a histogram. As a normalization procedure, a suitable family of distributions can be fit to the distribution. A parameterization of that distribution can be stored as a feature for downstream prediction of phenotype from data and feature engineering procedures.

The numbers of sequence reads classified as corresponding to certain biological sites (e.g., by comparing to sequences known to have specific functionality, which can act as an alignment) can be used to determine features in a similar manner as other values described herein. For example, number of reads corresponding to particular biological sites can be determined in windows. As another example, a feature can be a ratio of amounts of sequence reads across different biological sites. For instance, a ratio of TSS counts to genome body counts can be determined.

Similar to the above example a collection of all repeat elements and their families can be maintained from the DFAM database. Each read from a FASTQ can be stream and a dictionary of repeat family elements is used to query the read for membership. If identified, that repeat family element key can be enumerated.

Accordingly, specific biological events can be observed from or derived from sequence reads. For example, models for RNA splice sites, open reading frames, heterochromatin, and euchromatin can be used to quantify the number of predicted biological functional events of a particular type in a sequence read. As examples, such numbers of events per sequence read (or per window) can be used to generate features.

Further, biochemical, chemical, physical, or statistical mechanical properties of reads sequenced can be estimated from models or determined. For example, the charge distribution based on the known biochemical properties of nucleotides can be analyzed, as well as inferences of the steric or structural properties of those sequence reads.

4. Content and Complexity of the Collection of DNA Strings

Aggregate measures can be determined using the information content and complexity of the collection of DNA strings (sequence reads). For sequence complexity, it can include determining the percentages of different bases of a sequence read, how often a short sequence of bases repeat, and how often a single base repeats. The entropy of a collection of reads can be calculated by estimating the distribution of mutual information between each read within a collection of observed read sequences. This provides an aggregate measure of how much information, measured in bits, is obtained upon observing each additional read. String kernels, functions that can measured the relation be strings, can be applied to a collection of reads in order to estimate a covariance, or relation, matrix directly on the sequence reads themselves.

C. Measures of Relations Between Samples

Some features can be determined using differences (or other relationships) between or within samples. The differences may result from, but not limited to, an intervening lab process (e.g. enzymatic steps) or a passage of time between sampling points, or multiple samplings at the same time to reduce uncertainty. Such features can be referred to as comparison metrics (also referred to as delta changes), which are agents that might cause a change in relationship. The changes may result from a delta change agents (metric comparison agents) that are a source of such changes in genetic data. There are various ways to compute the comparison metrics, as is described herein.

A delta change agent can comprise any source that changes or may change the sample and/or resultant raw data arising from the sample, and whose changing pattern if detected may reveal signals to classify a phenotype or infer a treatment. In various embodiments, the delta change agents can comprise one or more of the following: an amount of time, biological process, a measurement of aging, a treatment, an experiment, a germline variation, a somatic mutation, a disease, a disease state, a deviation from a normal state, an enzymatic treatment step, a methylation step, a methylation sequencing step, nucleic acids of a particular biological type (class), and a method of enriching nucleic acids of a particular biological type. Examples of a time agent include a time: characterizing two biological conditions (e.g., a time gap refers to a 4-year period between two cancer stages), between sample collections (e.g., 24 hours between collecting two samples from a subject), a time between laboratory steps, such as addition of enzymes or use of physical or chemical enrichment steps that may alter the presence or intensity of signal. In various embodiments, a method of enriching a certain class of nucleic acids (e.g., ones classified by their sequence content, as described above) comprises one or more of the following: using a panel of primers, a hybridization-based approach, a filtration method, a size-selection method, a gel-based approach, a bead-based approach, and a pull-out method.

Such comparison metrics can include variants identified relative to a reference genome as they correspond to a metric obtained by a comparison of sequences. Above descriptions of how such values may be aggregated or otherwise processed also apply to comparison metrics. For example, an amount of comparison metrics within a window can be determined. As other examples, embodiments can determine a minimum, maximum, an average (e.g., a weighted average), or other property of a distribution of comparison metrics. Embodiments can normalize a measured distribution of features with respect to a number of total measured values within a sliding window. Calculating any of the statistical values can be repeated with randomly selected sliding windows The features resulting from the comparison metrics can be used in generating a feature vector in a manner as described above. This feature vector can be considered a change vector. Using two samples to compute such a change vector can allow detection of patterns that are unique to such differences.

As an example, two samples from a same subject can be obtained at two time points. Genetic data can be measured for both samples. Changes between the genetic data can be determined and used to create a change vector. For example, differences in a normalized read count for genomic windows can be determined.

More than one change vector can be used in a training of a model, e.g., based on a selected set of features that form a feature vector. The different change vectors can correspond to different parts of the overall feature vector, e.g., considered separate elements of the feature vector. For example, one element of the overall feature vector can be a change vector of read counts in windows, and another element of the overall feature vector can be a change vector corresponding to numbers of variants at different locations in a genome.

And, different change vectors can correspond to different delta change agents of a same type, e.g., comparisons between different pairs of samples, which may be taken at different time gaps.

As a real-world example, a patient with a rectal cancer is diagnosed having a lung cancer. However, the physician is not sure the lung cancer is a metastasis or a primary. A biopsy is performed to extract a tumor tissue and a normal tissue. The samples (i.e., the tumor tissue and the normal tissue) are sequenced. Embodiments can compare the DNA sequences across the samples in different biological conditions to identify delta changes in DNA sequences. The delta changes can be analyzed probabilistically to evaluate true nucleotide differences between tumor and normal states. These differences can be used to generate features for training the model, which can classify the lung cancer as a primary rather than a metastasis. As such, an appropriate treatment is taken by the physician

V. Selection of Input Features for Feature Vector

As described above, a large set of features can be generated to provide a feature space from which the feature vector can be determined. This feature vector can then be used for training a current version of the machine learning model. Such a process can be performed as described with respect to feature selection module 370 and training module 380 of FIG. 3.

Ideally, the feature selection can select features that are invariant within samples that have a same classification (e.g., have a same probability or associated risk of particular phenotype), but where such features vary among groups of samples that have different classifications. Procedures can be implemented to identify what features appear to be the most invariant within a particular population (e.g., one that shares a classification or lease has a similar classification when the classification is a real number). Procedures can also identify features that vary among populations. For example, read counts within various regions can be analyzed to determine how they change within a population and compare those numbers to separate population.

Various statistical metrics can be used to analyze the variation in a feature across populations for the purpose of selecting features that might be predictive of a classification, and thus would be advantageous for training. Further embodiments can also select a particular type of model based on the analysis of the feature space, and the selected features to be used in the feature vector.

A. Creation of Feature Vector

The feature vector can be created as any data structure that can be reproduced for each training sample, so that corresponding data appears in the same place in the data structure across the training samples. For example, the feature vector is associated with indices, where a particular value exists at each index. As explained above, a matrix can be stored at a particular index of the feature vector, and the matrix elements can have further sub-indices. Other elements of the feature vector can be generated from summary statistics of such a matrix.

As another example, a single element of a feature vector can correspond to the set of read counts across a set of windows of a genome. Thus, an element or the feature vector can itself be a vector. Such counts of reads can be of all reads or certain group (class) of reads, e.g., reads having a particular sequence complexity or entropy.

In some embodiments, an element of the feature vector can be the result of a concatenation of multiple features. This can differ from other examples where an element is itself an array (e.g., a vector or matrix) in that the concatenation value can be treated as a single value, as opposed to a collection of values. Thus, features can be concatenated, merged, and combined to be used as engineered features or feature representations for the machine learning model.

Multiple combinations and approaches to merging the features can be performed. For example, when different measures are counted over the same window (bin), ratios between those bins, such as inversions divided by deletions, could be a useful feature. Further, ratios of bins that are proximal in space and whose merging might convey biological information, such as dividing a transcript start site count by a gene body count, can also serve as a useful feature. Features can also be engineered, e.g., by setting up a multi-task unsupervised learning problem where the joint probability of all feature vectors given a set of parameters and latent vectors is maximized. The latent vectors of this probabilistic procedure often serve as excellent features when trying to predict phenotype (or other classifications) from biological sequence data.

B. Weights Used in Training

As depicted in FIGS. 5 and 6, weights can be applied to features when they are added to a feature vector. Such weights can be based on elements within the feature vector, or specific values within an element of the feature vector. For example, every region (window) in the genome can have a different weight. Some windows can have a weight of zero meaning that the window does not contribute to classification. Other windows can have larger weights, e.g., between 0 and 1. Thus, a weighting mask can be applied to the values for the features used to create the feature vector, e.g., different values of the mask to be applied to features for count, sequence complexity, frequency, sequence similarity in the population, etc.

In some embodiments, the training process can learn the weights to be applied. In this manner, one does not need to know any prior knowledge or biological insight into the data before the training process. The weights initially applied to features can be considered as part of a first layer of the model. Once a model has been trained and satisfies one or more specified criteria, the model can be used in a production run to classify a new sample. In such production runs, any features that have an initial weight of zero do not need to be calculated. Thus, the size of the feature vector can be reduced from training to production.

C. Selecting Features Between Training Iterations

As mentioned above, a training process may not produce a model that satisfies desired criteria. At such a point, feature selection may be performed again. The feature space may be quite large (e.g., 35 or 100 thousand) so the number of different possible permutations of difference features to use in the feature vector can be enormous. Certain features (potentially many) may belong to a same class (type), e.g., read counts in windows, ratios of counts from different regions, variants at different sites, etc. Further, the concatenation of features into a single element can further increase the number of permutations.

The new set of features can be selected based on information from the previous iteration of the training process. For example, weights associated with the features can be analyzed. These weights can be used to determine whether a feature should be kept or discarded. A feature associated with a weight or average weight greater than a threshold can be kept. A feature associated with a weight or average weight less than a threshold (same or different than for keeping) can be removed.

The selection of features and creation of a feature vector for training the model can repeat until one or more desired criteria are satisfied, e.g., a suitable quality metric for the model. Another criteria may be selecting a model with the best quality metric out of a set of models generated with different feature vectors. Accordingly, a model with the best statistical performance and generalizability in the ability to detect a phenotype from the data can be chosen. Further, a set of training samples can be used for training various models for different purposes, e.g., a classification of a condition, of a treatment, etc.

VI. Training of Machine Learning Model

Figure 8:
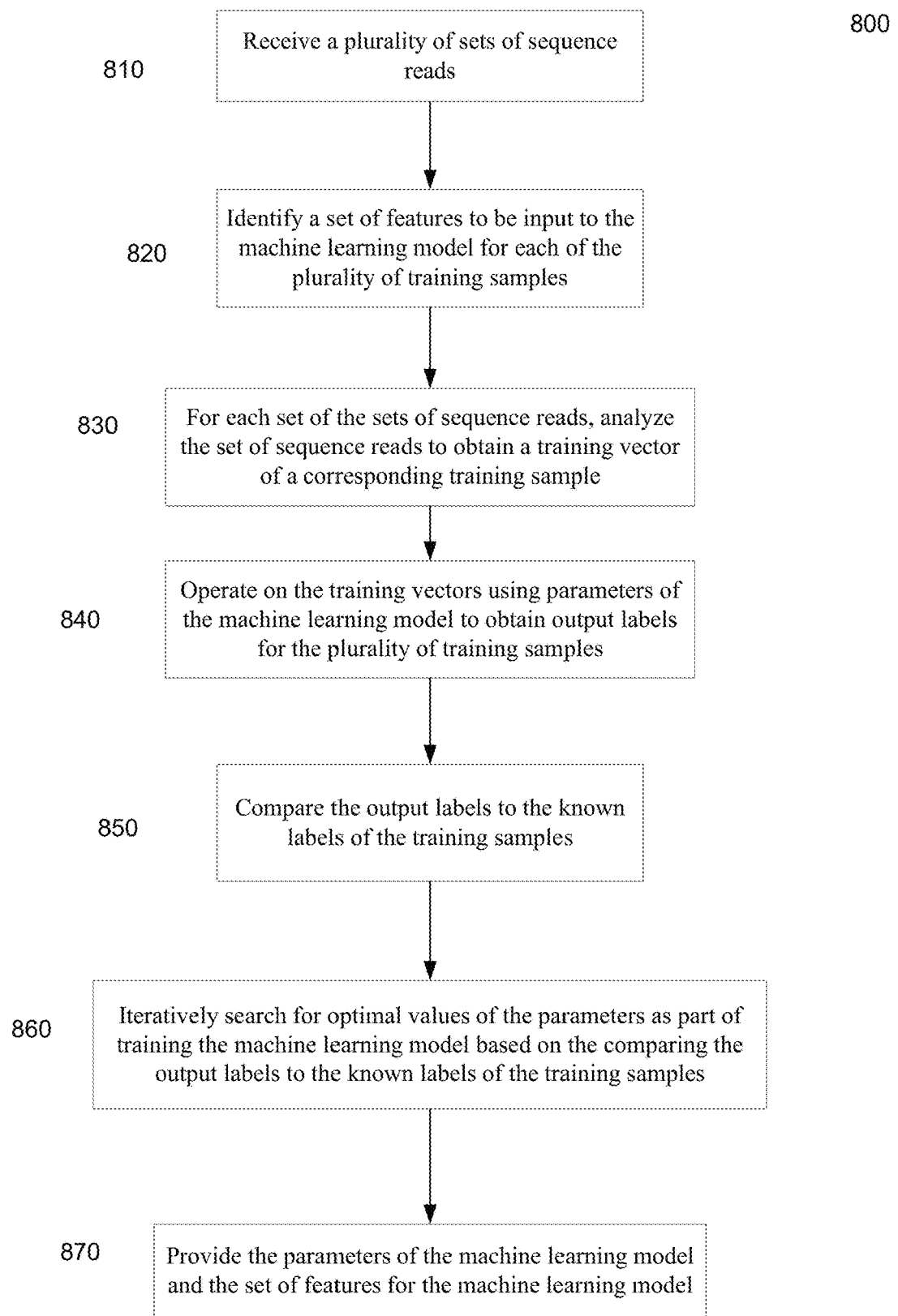
FIG. 8 is a flowchart of a method 800 of creating a machine learning model for performing classifications of biological samples according to embodiments of the present invention.

FIG. 8 is a flowchart of a method 800 of creating a machine learning model for performing classifications of biological samples according to embodiments of the present invention. Method 800 may be performed by a computer system.

At block 810, a plurality of sets of sequence reads is received. Each set of sequence reads can be generated from one of a plurality of training samples. One or more labels may be known for each of the training samples. The sequence reads may be obtained from any suitable technique, e.g., as described herein. The labels (e.g. condition of a subject) can be obtained via other techniques than analyzing genetic data, or via a known genetic signature.

At block 820, a set of features to be input to the machine learning model are identified for each of the plurality of training samples. As examples, the set of features can include aligned variables and/or non-aligned variables. The aligned variables can include one or more properties of a set of sequence reads in windows of a reference genome. The non-aligned variables can include statistical measures of occurrence of Kmers of a Kmer database in the set of sequence reads. Examples of aligned variable include a count of sequence reads aligned to each of a plurality of windows in a reference genome and a sequence similarity of sequence reads aligned to each of a plurality of windows in the reference genome.

At block 830, the following analysis is performed for each set of the sets of sequence reads. The set of sequence reads is analyzed to obtain a training vector of a corresponding training sample. The training vector can comprise values of the set of features for the set of sequence reads. Each element of the training vector can correspond to a feature that includes one or more variables. A feature of the training vector can comprise a matrix.

At block 840, the training vectors are operated on using parameters of the machine learning model to obtain output labels for the plurality of training samples. As examples, the operation of the parameters can include multiplication, addition, subtraction, division, and higher level functions, as may occur in logistic regression and neural networks, as well as other machine learning techniques.

At block 850, the output labels are compared to the known labels of the training samples. Comparing the output labels to the known labels of the training samples can provides an accuracy of the machine learning model at a given iteration of the training of the machine learning model. For example, a difference between the output labels and the known labels can provide a gradient (or other error measurement) of a cost function used in the training, where the gradient is used to determine how parameters of the machine learning model should be updated.

At block 860, a training process can iteratively search for optimal values of the parameters as part of training the machine learning model based on the comparing the output labels to the known labels of the training samples. As described herein, the set of features may not provide a sufficiently accurate model, even after training. In such a case, a new set of features can be selected for another iteration, thereby obtaining a new version of the machine learning model.

Accordingly, training the machine learning model can provide a first version of the machine learning model. Then, it can be determined whether the first version is acceptable. A quality metric can be determined for the first version, and the quality metric can be compared to one or more criteria (e.g., a threshold). It can be determined whether to select a new set of features based on the comparing of the quality metric to the one or more criteria. The quality metric can be determined using the comparing of the output labels to the known labels of the training samples.

Once it is determined that the quality metric does not satisfy the one or more criteria, a new set of features can be selected. New training vectors can be generated using the new set of features. The new training vectors can be operated on using the parameters of the machine learning model to obtain new output labels for the plurality of training samples. The new output labels can be compared to the known labels of the training samples, and a new iterative search can be performed.

At block 870, the parameters of the machine learning model and the set of features for the machine learning model are provided. The parameters and the set of features can form a definition of the model, which may be used for classifying a new subject. For example, a new set of sequence reads generated from a new sample, for which a label is not known, can be received. The set of features provided for the machine learning model can be identified, e.g., by reading from a file. The definition of the model can be stored in a sequencing instrument or an analyzer instrument in communication with the sequencing instrument. The new set of sequence reads can be analyzed to obtain a new training vector. The new training vector can be operated on using parameters of the machine learning model to obtain a new output label for the new sample.

VII. Use of Machine Learning Model

Figure 9:
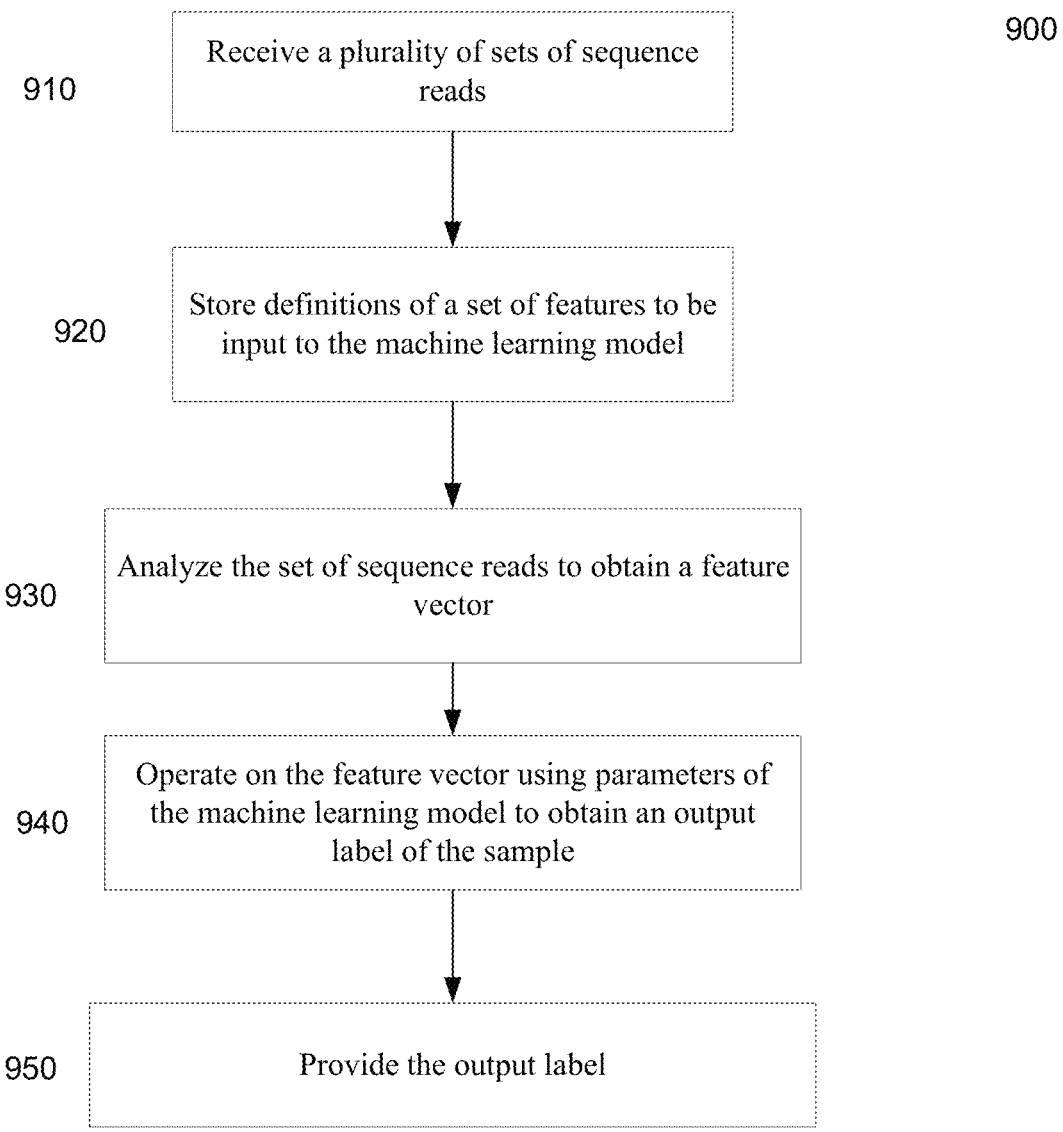
FIG. 9 is a flowchart of a method 900 of implementing a machine learning model for performing classifications of biological samples according to embodiments of the present invention.

FIG. 9 is a flowchart of a method 900 of implementing a machine learning model for performing classifications of biological samples according to embodiments of the present invention. Method 900 may be performed by a computer system. Description of functionality for method 900 can also be applied to method 800/

At block 910, a set of sequence reads generated from a sample is received. As for method 800, the sequence reads can be received at a computer system, which can be communicably coupled with a sequencing instrument that generated the reads.

At block 920, definitions of a set of features to be input to the machine learning model are stored. As examples, the set of features can include aligned variables and/or non-aligned variables. The aligned variables can include one or more properties of a set of sequence reads in windows of a reference genome. The non-aligned variables can include statistical measures of occurrence of Kmers of a Kmer database in the set of sequence reads.

At block 930, the set of sequence reads are analyzed to obtain a feature vector. The feature vector can comprise values of the set of features for the set of sequence reads. Each element of the feature vector can correspond to a feature that includes one or more variables. The generation of the feature vector can be performed in a variety of way, as is described herein, e.g., in sections III and IV.

In some embodiments, sequence reads can be assigned to a particular class based on their sequence content (e.g., relating to a Kmer distribution or sequence complexity). In one implementation, at least a partial sequence (e.g., as determined by a sliding window over the read) of a sequence read can be compared to one or more sequence tables. Each sequence table can correspond to a different class of sequence reads, e.g., protein binding sites, TSS sites, and others described herein. The sequence read can be assigned to one or more classes of sequence reads based on the comparison, e.g., whether the sequence read sufficiently matched to one of the sequences in one of the sequence tables (e.g., having less than a maximum number of mismatches). One or more features can be determined for each of the classes of sequence reads based on the sequence reads of that class. Such a feature may not be determined using sequence reads of at least one of the other classes, and potentially not of any of the other classes. In some implementations, a read of a particular class may be removed from determination of a feature, or it can be determined not to align the sequence read.

Analyzing the set of sequence reads to obtain the feature vector can include identifying a set of somatic variants, as is described herein. Sequence reads of the sample (e.g., plasma or serum) can be compared to a genome of the subject (e.g., as determined from white blood cells). The sequence reads corresponding to the somatic variants can be used to determine one or more features corresponding to the set of somatic variants, e.g., a feature that specifically uses the reads having somatic variants. Similarly, germline variants can be determined by comparing sequence reads generated from a separate sample of the subject to a reference genome, and the germline variants can be used to determine one or more features corresponding to the set of germline variants.

In one embodiment, the set of input features include the statistical value measuring the occurrence of Kmers of the Kmer database in the set of sequence reads. In such an embodiment, partial sequences of a sequence read can be compared to Kmers of a Kmer database to determine a Kmer histogram of Kmer occurrences for each of the reads, e.g., as described herein. The Kmer histograms can be used to determine at least one of the set of features. For example, a distance between each pair of Kmer histograms can be determined to form a Kmer covariance matrix. The Kmer covariance matrix can be used to determine the at least one of the set of features.

After an initial set of features is determined, the initial set of features can be transformed to reduce a number of features in the set of features. Examples of such transformations and other transformations are provide elsewhere in this disclosure.

Referring back to FIG. 9, at block 940, the feature vector is operated on by parameters of the machine learning model to obtain an output label of the sample. For example, the feature vector can be input to the machine learning model, which can use the parameters to obtain the output label.

At block 950, the output label can be provided, e.g., as an output of a computer system. As another example, the output label can be provided to a module for further processing. Such further processing can result in a measurement system performing further measurements on the sample or another sample from a same subject.

VIII. Results

The following results illustrate examples of implementations of embodiments of the present invention.

A. Classifications of Cancers

Figure 10A:
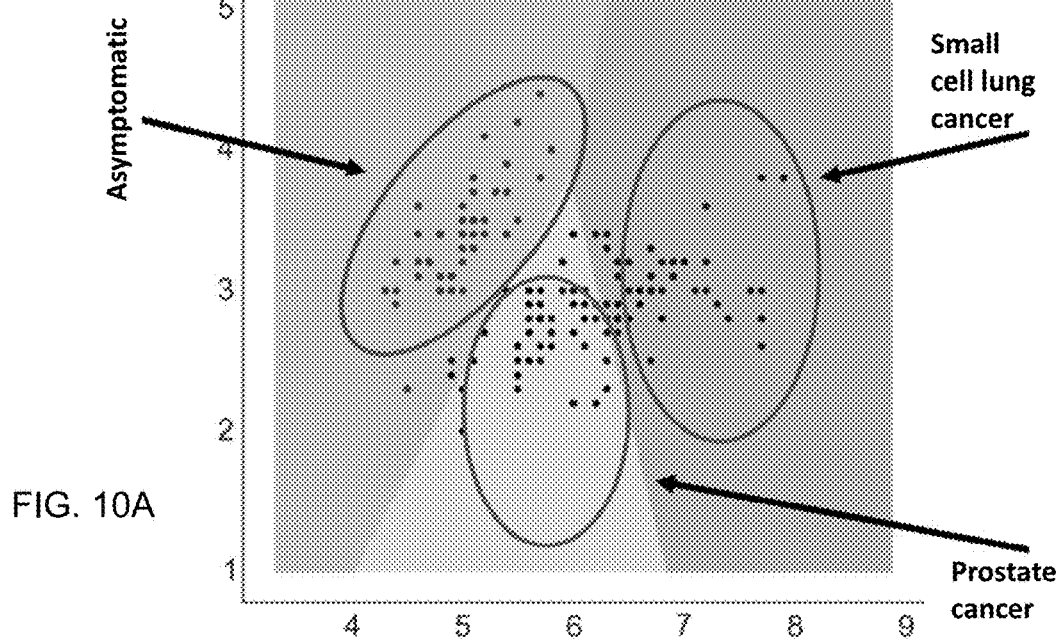
FIG. 10A illustrates an example of classifiers to distinguish asymptomatic samples, prostate cancers, and small cell lung cancers.
Figure 10B:
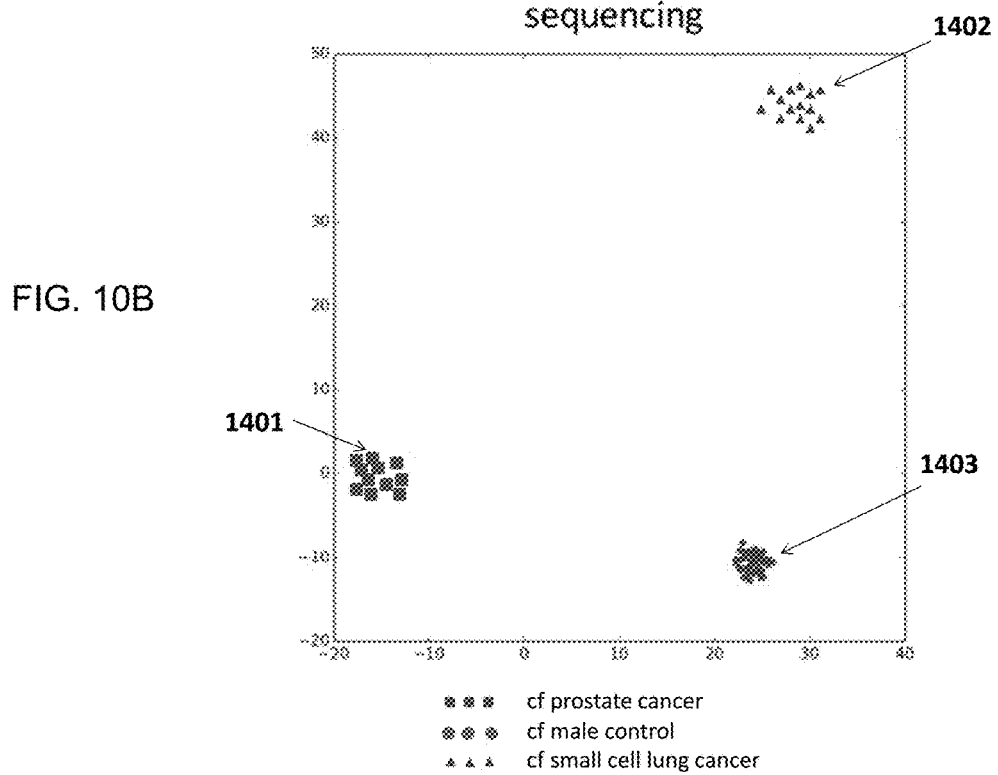
FIG. 10B illustrates an example of a spatial representation of asymptomatic samples, prostate cancers, and small cell lung cancers.

FIG. 10A illustrates an example classification system developed to distinguish asymptomatic samples, prostate cancers, and small cell lung cancers. After feature identification and feature reduction are performed, a spatial representation of data points can be visualized, such as FIG. 10B which plots prostate cancers 1401, small cell lung cancers 1402, and male controls 1403 in a 2D space.

Figure 11A:
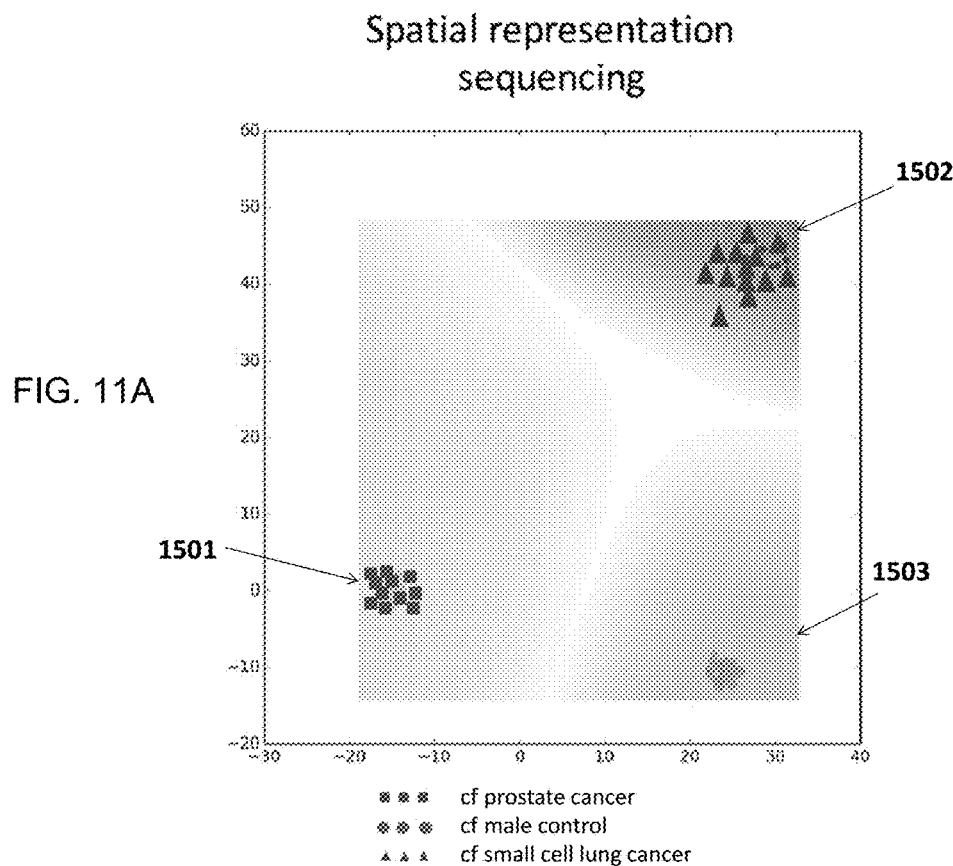
FIG. 11A illustrates an example of a spatial representation of data samples with classifier probabilities superimposed at the background.

Next, a deep learning algorithm is applied to identify the boundaries between three types of classes. FIG. 11A shows a spatial representation of the data samples with classifier probabilities superimposed at the background. An initial analysis determines that the left region 1501 belongs to prostate cancers, the top right region 1502 belongs to small cell lung cancers, and the bottom right region 1503 belongs to male controls. Nevertheless, the classification regions may be overestimated, and the deep learning algorithm further evaluates the regions with a higher accuracy and generates results shown in FIG. 11B where regions densely capturing data samples are plotted: a left bottom region 1601 belongs to prostate cancers, a top right region 1602 belongs to small cell lung cancers, and a bottom right region 1603 belongs to male controls.

Figure 11B:
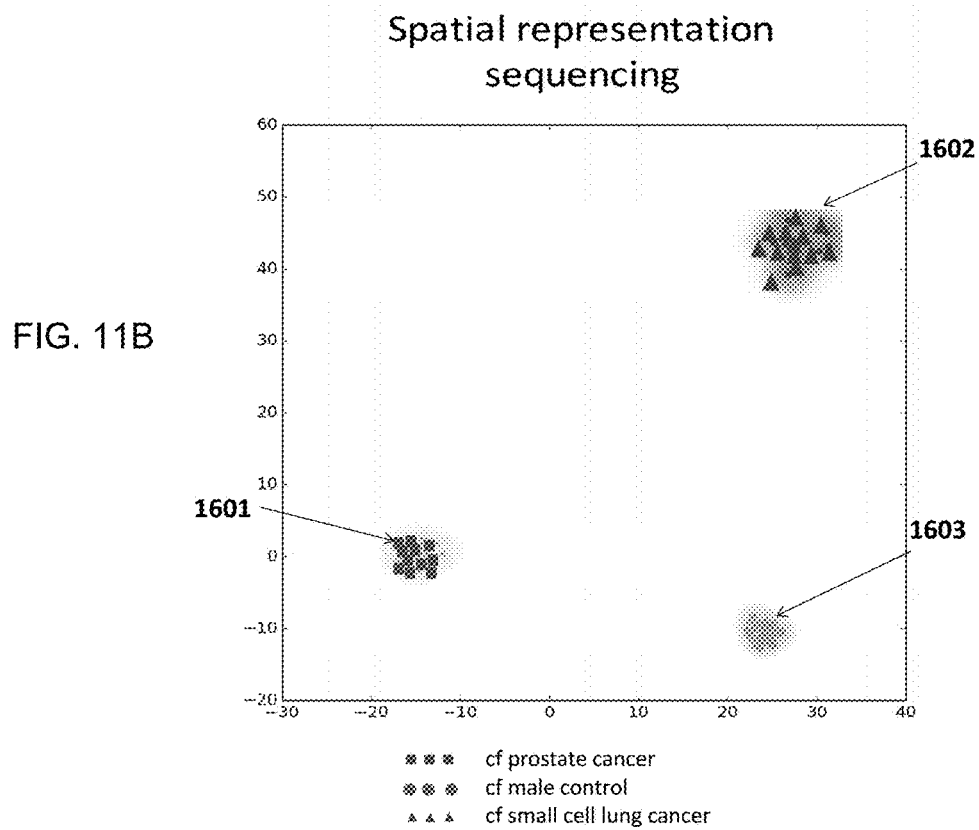
FIG. 11B illustrates an example of a spatial representation of data samples with high classification probabilities superimposed at the background.
Figure 12A:
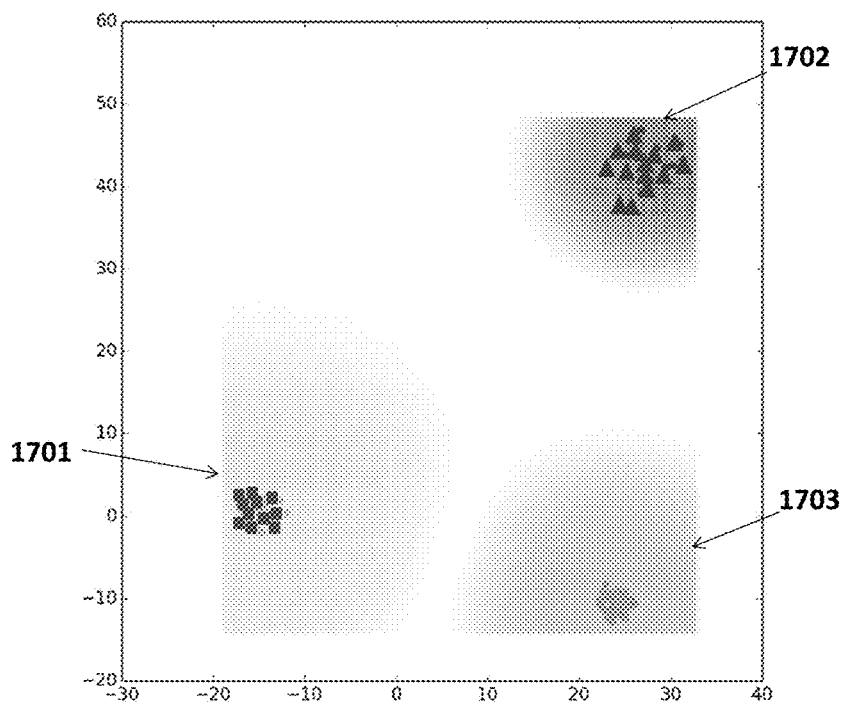
FIG. 12A illustrates an example of a spatial representation of data samples with classification probabilities generated from deep learning analysis.
Figure 12B:
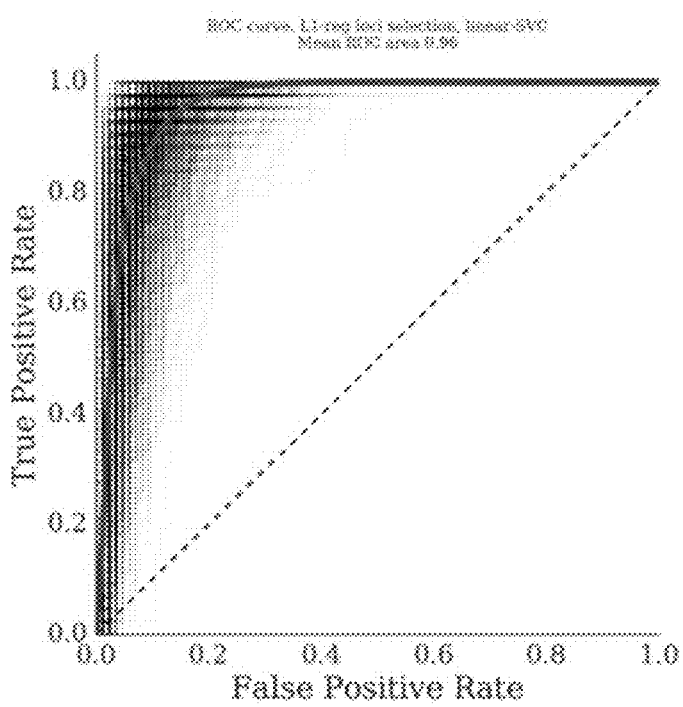
FIG. 12B illustrates an example of performance measurement of classifying asymptomatic samples, prostate cancers, and small cell lung cancers.

The regions defined by FIG. 11B may over-fit to given data samples. Thus, the deep learning algorithm is further reevaluate the classification boundaries and redefine optimal regions, as shown in FIG. 12A where a left bottom corner 1701 belongs to prostate cancers, a top right corner 1702 belongs to small cell lung cancers, and a bottom right corner 1703 belongs to male controls. Based on the derived classifiers in FIG. 12A, performance evaluation is shown in FIG. 12B where a mean ROC area of 0.96 is achieved.

B. Molecular Age Determination

Figure 13A:
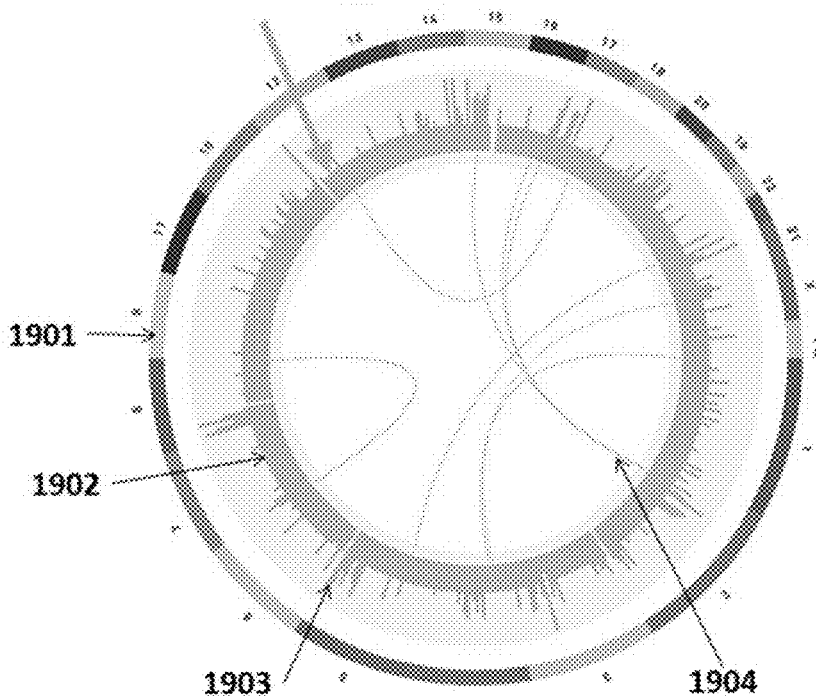
FIG. 13A illustrates an example of a ring representation of a genome.

The technologies disclosed herein are able to classify or predict more phenotypes, such as age. FIG. 13A visualizes a genome of a subject. The visualization comprises two rings. The outer ring 1901 indicates chromosomes of the genome, and the inner ring 1902 denotes stability of DNA. A spike 1903 at a chromosomal locus indicates instability of the locus. For example, the values in inner ring 1902 can correspond to counts of variants within bins (windows) of the genome, as corresponding to outer ring 1901.

Figure 13B:
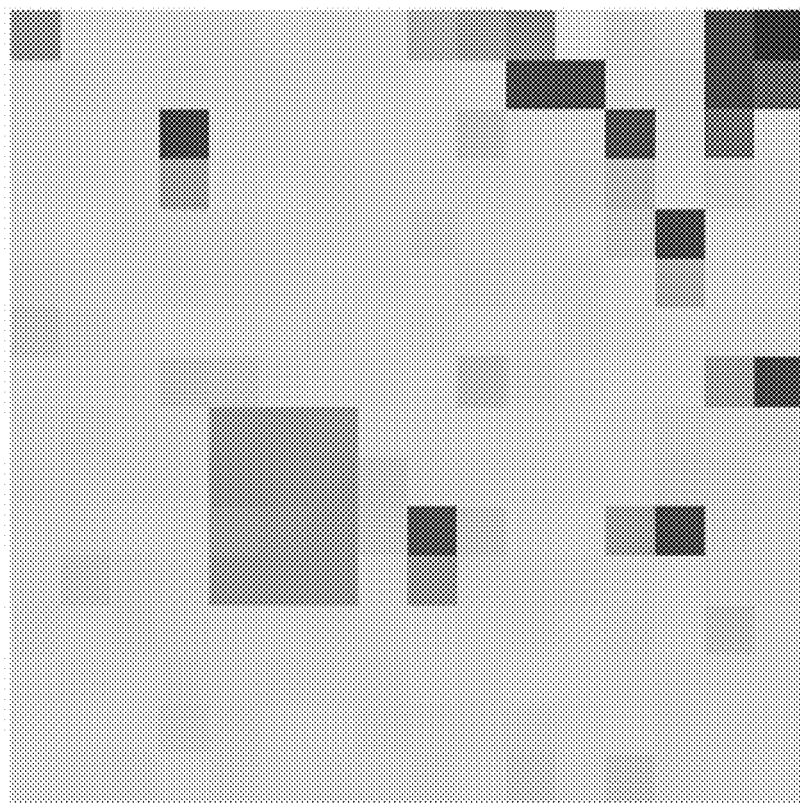
FIG. 13B illustrates an example of a Cartesian representation of a genome.

A wire 1904 connecting two chromosomal loci indicates a fusion. The fusion results from two sequences corresponding to the ends of a DNA molecule mapping to different regions of the genome, e.g., sufficient far apart (e.g., greater than 1 Mb, 10 Mb, or 50 Mb apart, including on different chromosomes. The visualization allows a user to see DNA stability of a subject. A smooth ring means a more stable DNA architecture. Further, the genome can be visualized on a square plot, as shown in FIG. 13B where a pixel intensity denotes stability of a DNA architecture. Ideally, smooth pixel intensities imply more stable DNA architectures.

Figure 14A:
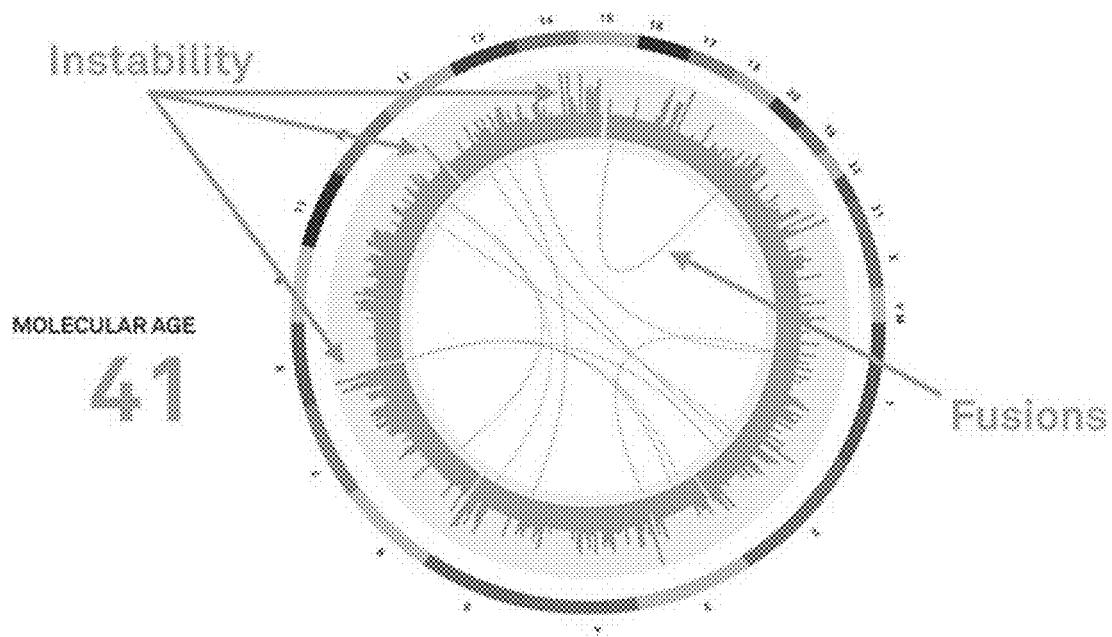
FIG. 14A illustrates an example of a ring representation of a genome with a molecular age of 41.
Figure 14B:
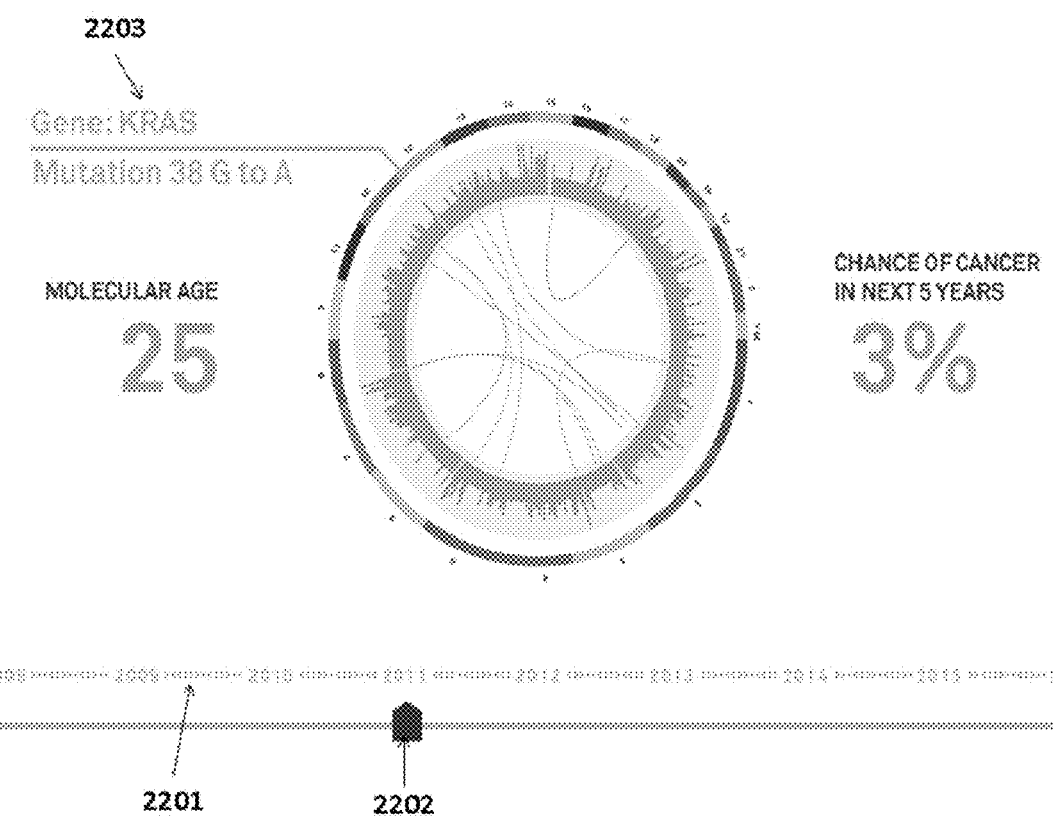
FIG. 14B illustrates an example of a ring representation of a genome with a molecular age of 25.

FIG. 14A illustrates a DNA ring plot of a subject. In this case, analysis identifies that the molecular age is 41, which is an examples output classification that may be obtained from a machine learning model. FIG. 14B further shows detailed information of the subject. The figure comprises a time axis 2201, where a curser 2202 can be moved along the time axis to visualize biological conditions in the time domain. When a time is set to the year of 2011, the molecular age of 25-year-old is shown. In addition, a mutation 2203 at gene KRAS is shown. Overall, the system predicts that the subject has a 3% chance getting a cancer in the following 5 years. This chance of getting cancer is another example of an output classification of a machine learning model according to embodiments.

Figure 15A:
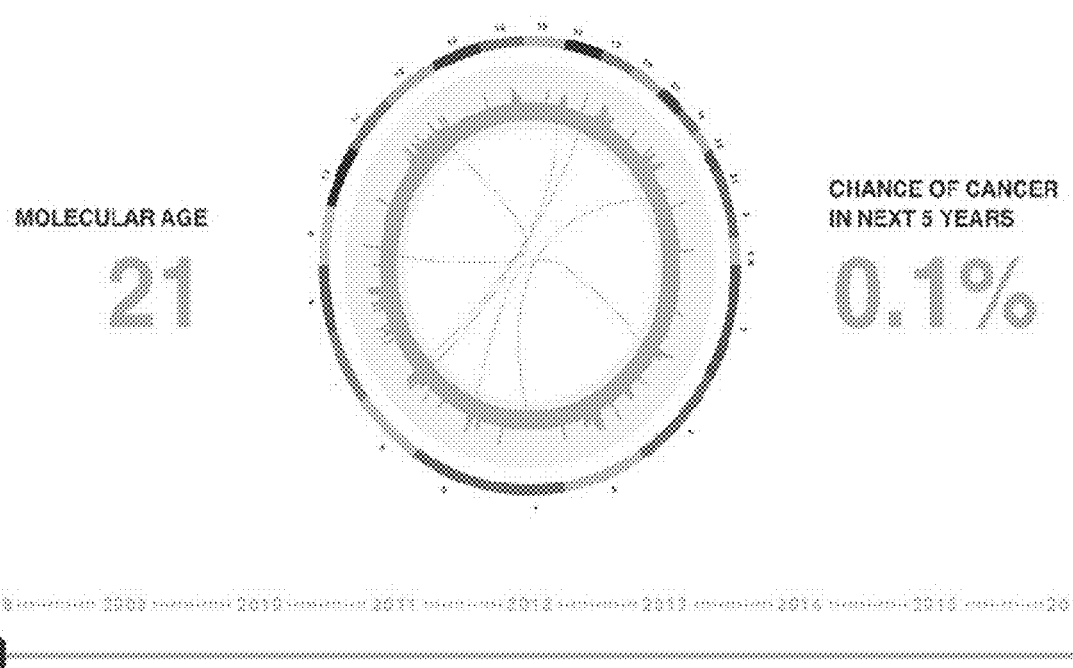
FIG. 15A illustrates an example of a ring representation of a genome with a molecular age of 21.
Figure 15B:
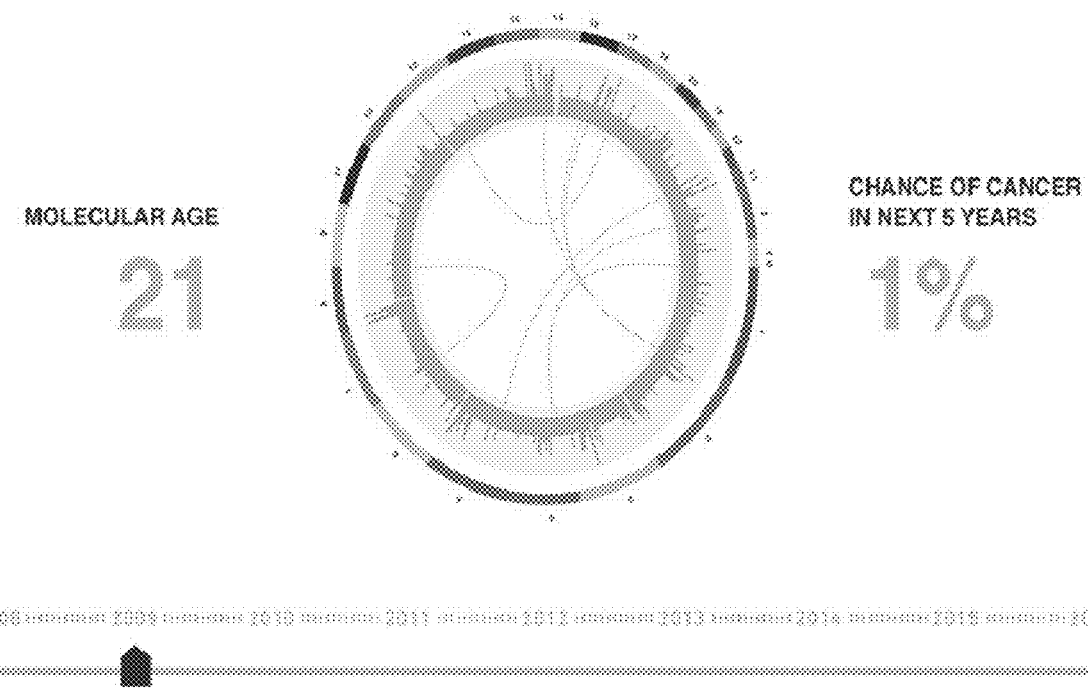
FIG. 15B illustrates an example of a ring representation of a genome with a molecular age of 21.
Figure 16A:
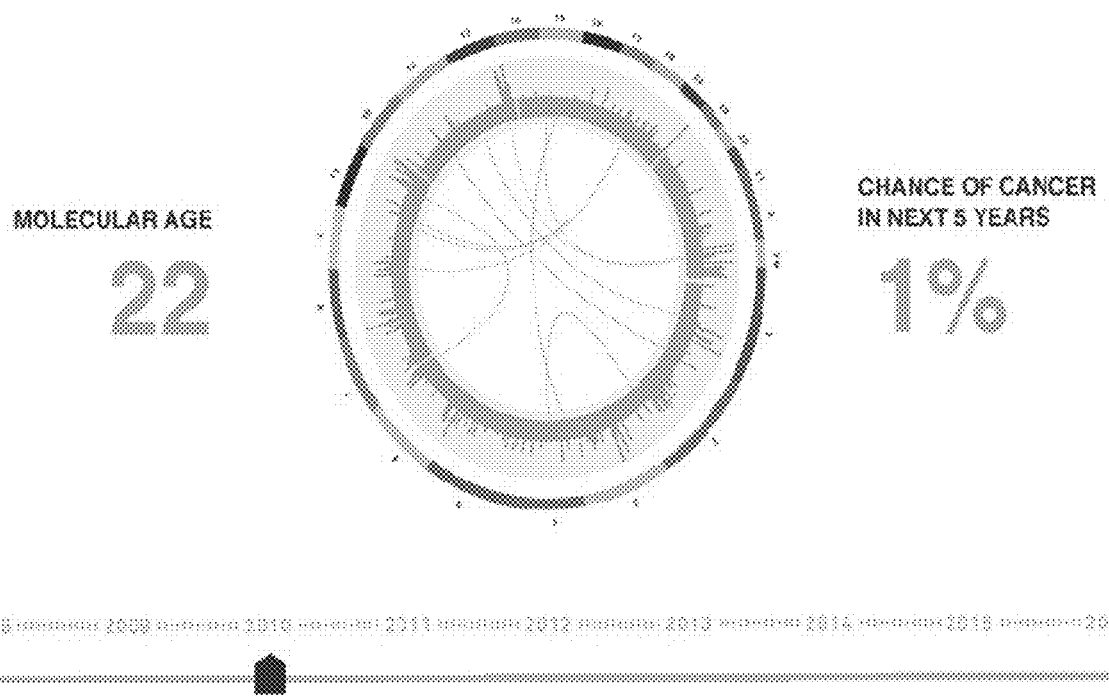
FIG. 16A illustrates an example of a ring representation of a genome with a molecular age of 22.
Figure 16B:
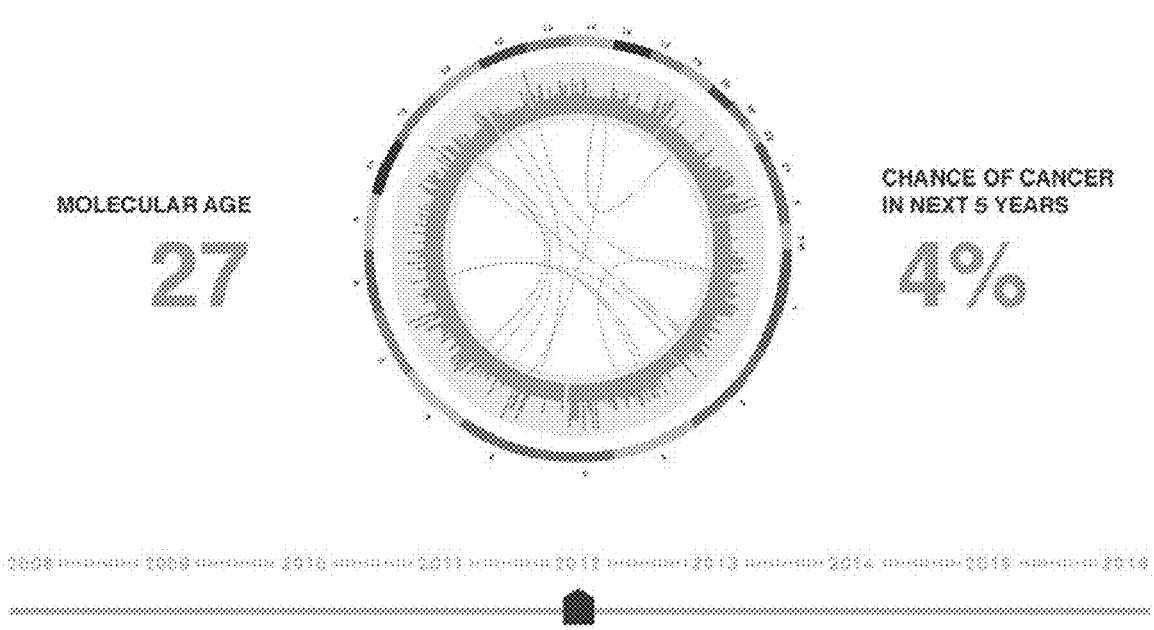
FIG. 16B illustrates an example of a ring representation of a genome with a molecular age of 27.

FIG. 15A shows the genomic information of the subject in the year of 2008, wherein the molecular age is determined as 21 with a 0.1% chance of getting cancers in the following 5 years. FIG. 15B shows the genomic information of the subject in the year of 2009, wherein the molecular age is determined as 21 with a 1% chance of getting cancers in the following 5 years. FIG. 16A shows the genomic information of the subject in the year of 2010, wherein the molecular age is determined as 22 with a 1% chance of getting cancers in the following 5 years. FIG. 16B shows the genomic information of the subject in the year of 2012, wherein the molecular age is determined as 27 with a 4% chance of getting cancers in the following 5 years.

Figure 17A:
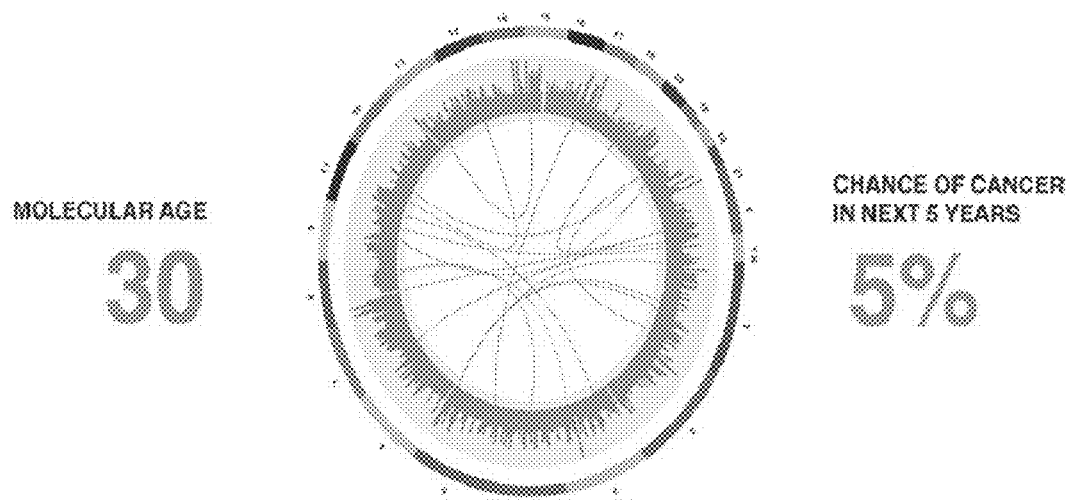
FIG. 17A illustrates an example of a ring representation of a genome with a molecular age of 30.
Figure 17B:
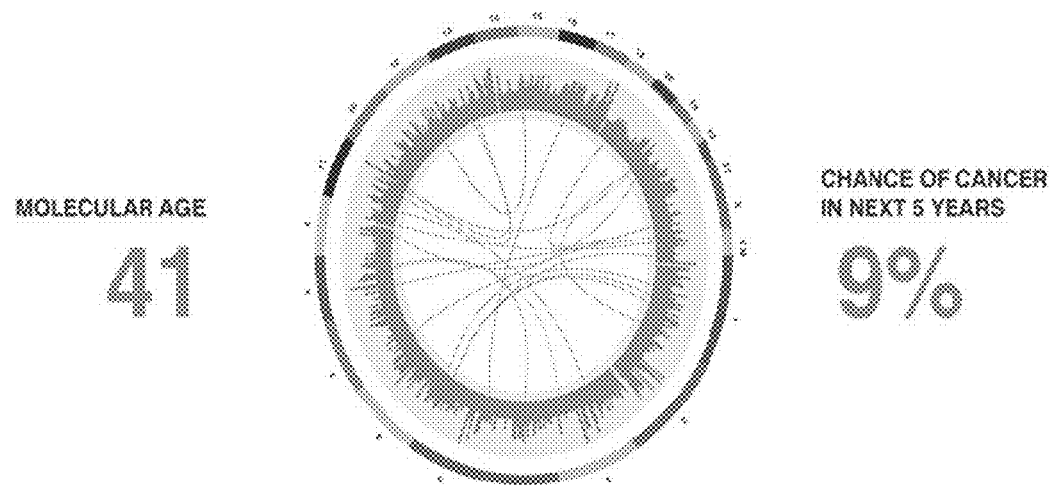
FIG. 17B illustrates an example of a ring representation of a genome with a molecular age of 41.
Figure 18A:
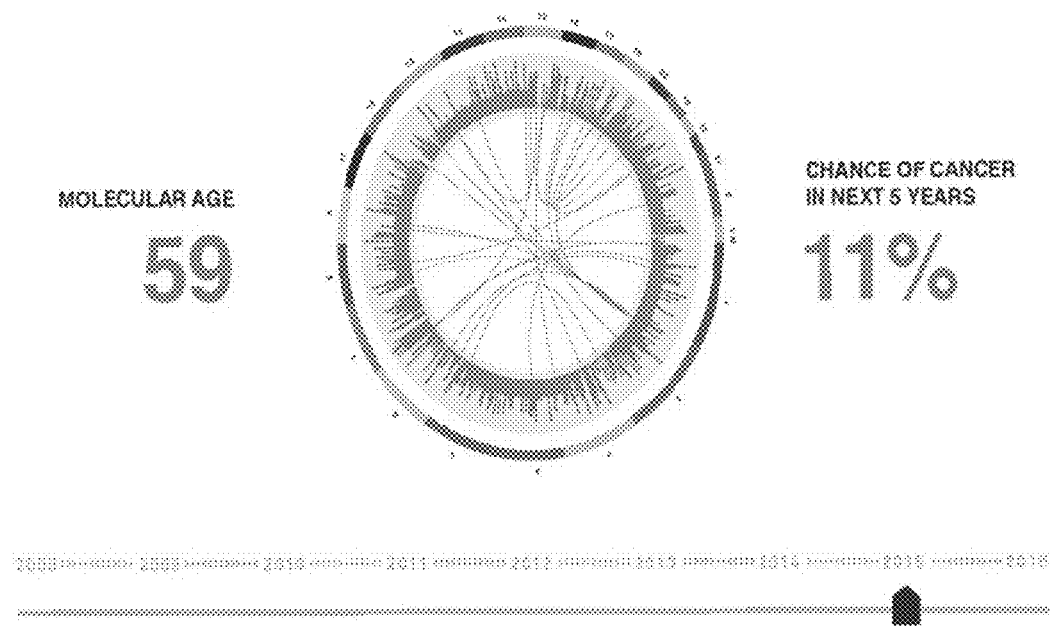
FIG. 18A illustrates an example of a ring representation of a genome with a molecular age of 59.

FIG. 17A shows the genomic information of the subject in the year of 2013, wherein the molecular age is determined as 30 with a 5% chance of getting cancers in the following 5 years. FIG. 17B shows the genomic information of the subject in the year of 2014, wherein the molecular age is determined as 41 with a 9% chance of getting cancers in the following 5 years. FIG. 18A shows the genomic information of the subject in the year of 2015, wherein the molecular age is determined as 59 with a 11% chance of getting cancers in the following 5 years.

C. Prostate Cancer

Figure 18B:
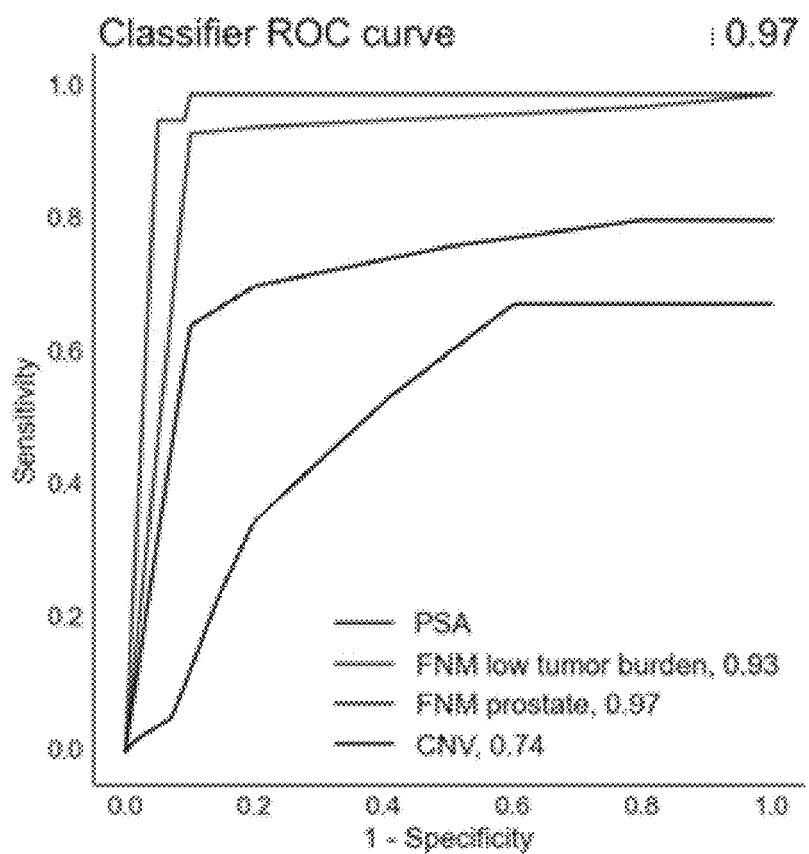
FIG. 18B shows example classifier results for prostate according to embodiments of the present invention.

FIG. 18B shows example classifier results for prostate according to embodiments of the present invention. In a cancer diagnostics study of high (n=262) and low tumor burden (n=89) prostate cancer with age-matched, disease-negative controls (n=50), a classifier model of an embodiment (FNM prostate) achieved ROC curve AUCs of 0.97 for late-stage and 0.93 for early-stage, low tumor burden prostate cancer detection. The classifier demonstrated superiority over traditional copy number variation profiling (ROC curve AUC of 0.74). These ROC curves were generated from 5-fold cross validation of the final step of our training/testing step.

IX. Example Systems

Figure 19:
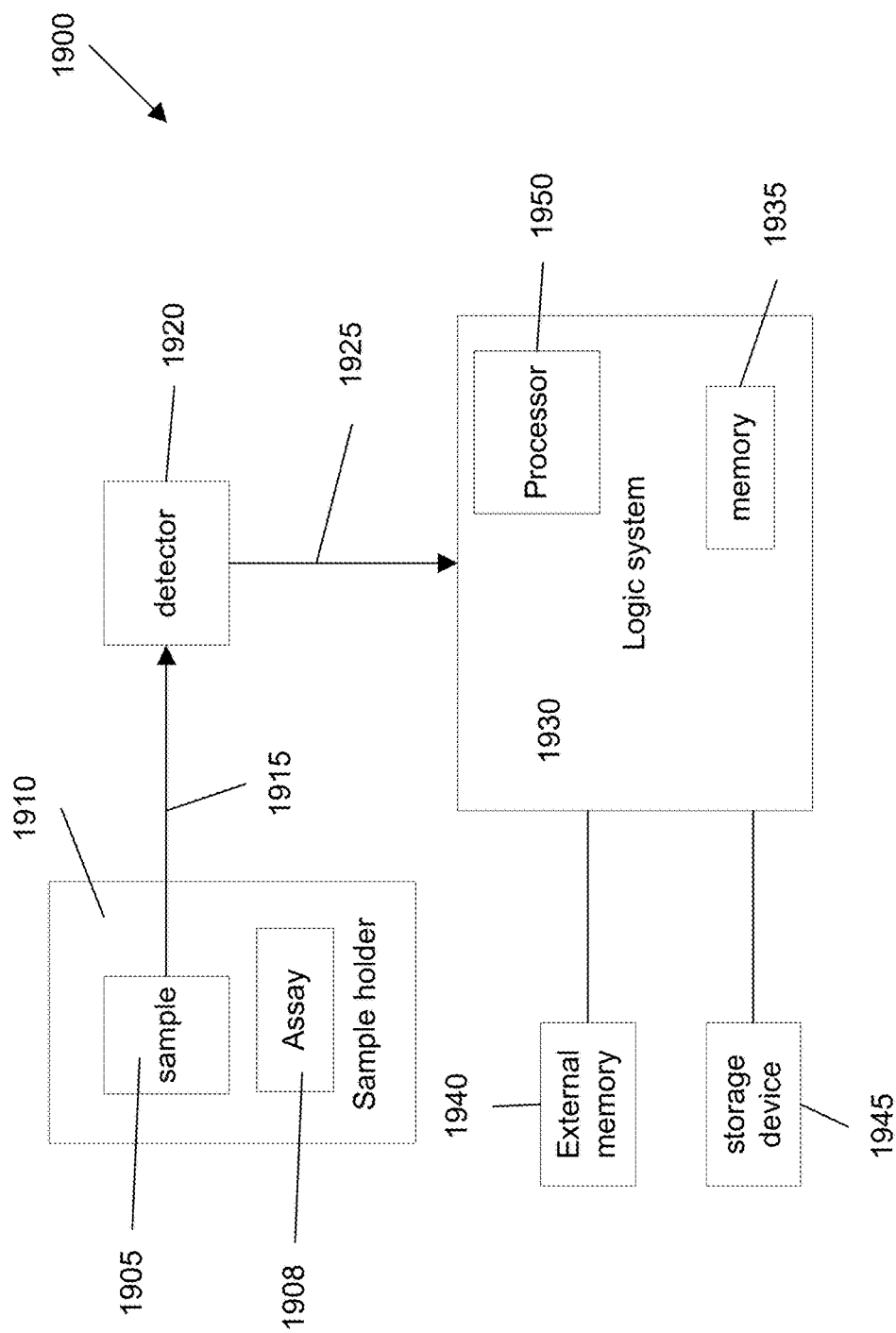
FIG. 19 illustrates a measurement system 1000 according to an embodiment of the present invention.

FIG. 19 illustrates a measurement system 1900 according to an embodiment of the present invention. The system as shown includes a sample 1905, such as cell-free DNA molecules within a sample holder 1910, where sample 1905 can be contacted with an assay 1908 to provide a signal of a physical characteristic 1915. An example of a sample holder can be a flow cell that includes probes and/or primers of an assay or a tube through which a droplet moves (with the droplet including the assay). Physical characteristic 1915, such as a fluorescence intensity value, from the sample is detected by detector 1920. Detector can take a measurement at intervals (e.g., periodic intervals) to obtain data points that make up a data signal. In one embodiment, an analog to digital converter converts an analog signal from the detector into digital form at a plurality of times. A data signal 1925 is sent from detector 1920 to logic system 1930. Data signal 1925 may be stored in a local memory 1935, an external memory 1940, or a storage device 1945.

Logic system 1930 may be, or may include, a computer system, ASIC, microprocessor, etc. It may also include or be coupled with a display (e.g., monitor, LED display, etc.) and a user input device (e.g., mouse, keyboard, buttons, etc.). Logic system 1930 and the other components may be part of a stand-alone or network connected computer system, or they may be directly attached to or incorporated in a thermal cycler device. Logic system 1930 may also include machine learning model and any described module that executes in a processor 1950.

Figure 20:
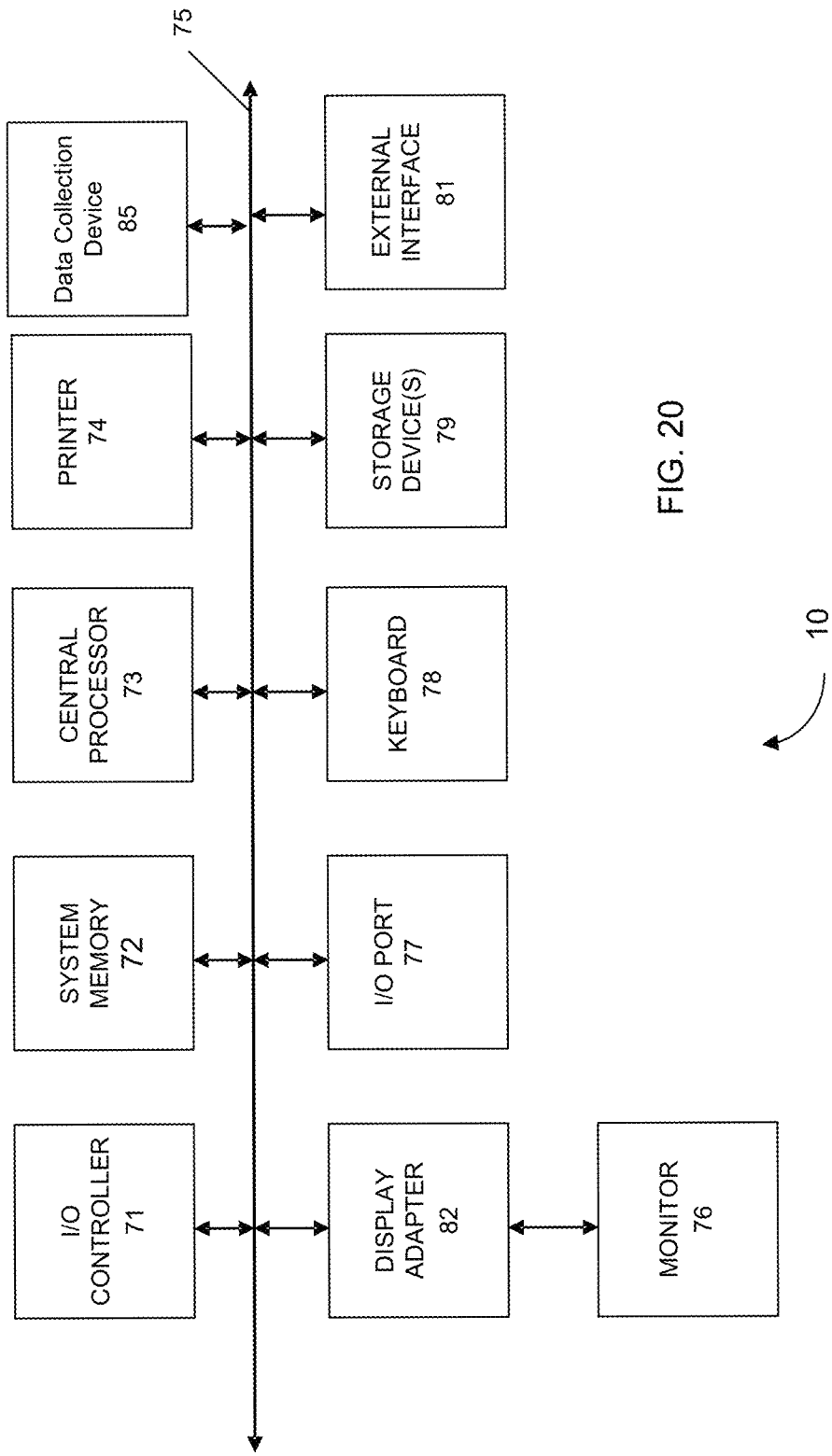
FIG. 20 shows a block diagram of an example computer system usable with system and methods according to embodiments of the present invention.

Any of the computer systems mentioned herein may utilize any suitable number of subsystems. Examples of such subsystems are shown in FIG. 20 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 20 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated. The term "based on" is intended to mean "based at least in part on."

All patents, patent applications, publications, and descriptions mentioned herein are incorporated by reference in their entirety for all purposes. None is admitted to be prior art.

What is claimed is:

1. A method of creating a machine learning model for a detection of cancer in a biological sample, the method comprising:
receiving a plurality of training samples, wherein each of the plurality of training samples is a biological sample obtained from a corresponding human subject having cancer and includes nucleic acids of the corresponding human subject;
for each of the plurality of training samples:
sequencing nucleic acids of the corresponding human subject to obtain a set of sequence reads, thereby obtaining a plurality of sets of sequence reads corresponding to a plurality of chromosomes; and
obtaining a known label for the detection of cancer for the corresponding human subject;
receiving, at a computer system, the plurality of sets of sequence reads of nucleic acids of the corresponding human subjects and the known labels for the detection of cancer;
identifying a set of features to be input to the machine learning model for each of the plurality of training samples, the set of features including non-aligned variables, the non-aligned variables including statistical measures of occurrence of Kmers of a Kmer database in the set of sequence reads;
for each set of the sets of sequence reads:
analyzing the set of sequence reads to obtain a training vector of a corresponding training sample, wherein the training vector comprises values of the set of features for the set of sequence reads, each element of the training vector corresponding to a feature that includes one or more variables;
operating on the training vectors using parameters of the machine learning model to obtain output labels for the detection of cancer for the plurality of training samples;
comparing the output labels to the known labels of the training samples;
iteratively searching for optimal values of the parameters as part of training the machine learning model based on the comparing the output labels to the known labels of the training samples; and
providing the parameters of the machine learning model and the set of features for the machine learning model.

2. The method of claim 1, wherein comparing the output labels to the known labels of the training samples provides an accuracy of the machine learning model at a given iteration of the training of the machine learning model.

3. The method of claim 1, wherein the set of features further includes aligned variables, the aligned variables including one or more properties of a set of sequence reads in windows of a human reference genome, and wherein the set of features includes a sequence similarity of sequence reads aligned to each of the windows of the human reference genome.

4. The method of claim 1, wherein a feature of the training vector comprises a matrix.

5. The method of claim 1, wherein training the machine learning model provides a first version of the machine learning model, the method further comprising:
determining a quality metric of the first version;
comparing the quality metric to one or more criteria; and
determining whether to select a new set of features based on the comparing of the quality metric to the one or more criteria.

6. The method of claim 5, further comprising:
determining that the quality metric does not satisfy the one or more criteria;
selecting the new set of features;
generating new training vectors using the new set of features;

operating on the new training vectors using the parameters of the machine learning model to obtain new output labels for the plurality of training samples;
comparing the new output labels to the known labels of the training samples; and
iteratively searching for the optimal values of the parameters as part of training the machine learning model based on the comparing the new output labels to the known labels of the training samples.

7. The method of claim 5, wherein the quality metric is determined using the comparing of the output labels to the known labels of the training samples.

8. The method of claim 1, further comprising:
receiving a new set of sequence reads generated from a new sample for which a label is not known;
identifying the set of features provided for the machine learning model;
analyzing the new set of sequence reads to obtain a new training vector; and
operating on the new training vector using the parameters of the machine learning model to obtain a new output label for the new sample.

9. The method of claim 1, wherein the detection is of lung cancer.

10. The method of claim 1, wherein the training samples include cell-free nucleic acids.

11. The method of claim 1, wherein the plurality of training samples comprise (i) human cell samples, (ii) human solid tissue samples, (iii) human liquid tissue samples, or (iv) other human cell-free material samples.

12. A method of implementing a machine learning model for detecting cancer in a biological sample, the method comprising:
sequencing nucleic acids of a human subject to obtain a set of sequence reads generated from a sample from the human subject, the set of sequence reads corresponding to a plurality of chromosomes;
storing definitions of a set of features to be input to the machine learning model, the set of features including non-aligned variables, the non-aligned variables including statistical measures of occurrence of Kmers of a Kmer database in the set of sequence reads;
analyzing the set of sequence reads to obtain a feature vector, wherein the feature vector comprises values of the set of features for the set of sequence reads, each element of the feature vector corresponding to a feature that includes one or more variables;
operating on the feature vector using parameters of the machine learning model to obtain an output label of the sample, wherein the output label comprises detection of cancer for the sample; and
providing the output label.

13. The method of claim 12, wherein analyzing the set of sequence reads to obtain the feature vector includes:
for each sequence read of a plurality of the set of sequence reads:
comparing at least a partial sequence of the sequence read to one or more sequence tables, each sequence table corresponding to a different class of sequence reads; and
assigning the sequence read to one or more classes of sequence reads; and
determining one or more features for each of the classes of sequence reads based on the sequence reads of that class and not sequence reads of at least one of the other classes.

14. The method of claim 12, wherein analyzing the set of sequence reads to obtain the feature vector includes:
for each sequence read of a plurality of the set of sequence reads:
comparing at least a partial sequence of the sequence read to one or more sequence tables, each sequence table corresponding to a different class of sequence reads;
assigning the sequence read to one or more classes of sequence reads; and
based on the one or more classes assigned to the sequence read, determining at least one of: removal of the sequence read for use in determining a feature and not to align the sequence read to a reference genome.

15. The method of claim 12, wherein analyzing the set of sequence reads to obtain the feature vector includes:
identifying a set of somatic variants by comparing sequence reads of the sample to a genome of the human subject; and
using the sequence reads corresponding to the set of somatic variants to determine one or more features corresponding to the set of somatic variants.

16. The method of claim 15, wherein analyzing the set of sequence reads to obtain the feature vector includes:
identifying a set of germline variants by comparing sequence reads generated from a separate sample of the human subject to a human reference genome; and
using the sequence reads corresponding to the set of germline variants to determine one or more features corresponding to the set of germline variants.

17. The method of claim 12, wherein analyzing the set of sequence reads to obtain the feature vector includes:
determining an initial set of features; and
transforming the initial set of features to reduce a number of features in the set of features.

18. The method of claim 12, wherein the set of features further includes aligned variables, the aligned variables including one or more properties of a set of sequence reads in windows of a reference genome, and wherein the set of features includes a sequence similarity of sequence reads aligned to each of the windows of the reference genome.

19. The method of claim 12, wherein the detection is of lung cancer.

20. The method of claim 12, wherein analyzing the set of sequence reads to obtain the feature vector includes:
for each sequence read of a plurality of the set of sequence reads:
comparing a plurality of partial sequences of the sequence read to Kmers of the Kmer database to determine a Kmer histogram of Kmer occurrences for each of the sequence reads; and
using the Kmer histograms to determine at least one of the set of features.

21. The method of claim 20, wherein using the Kmer histograms to determine at least one of the set of features includes:
determining a distance between each pair of Kmer histograms to form a Kmer covariance matrix; and
using the Kmer covariance matrix to determine the at least one of the set of features.

22. The method of claim 12, wherein the biological sample includes cell-free nucleic acids.

23. The method of claim 12, wherein the set of features further includes aligned variables, the aligned variables including one or more properties of a set of sequence reads in windows of a reference genome.

24. The method of claim 12, further comprising providing a recommendation to alter a biological condition based on the output label.

25. The method of claim 12, wherein the output label corresponds to a severity of a cancer of the human subject or a cancer status of the human subject.

26. A computer product comprising a non-transitory computer readable medium storing a plurality of instructions, that when executed on one or more processors of a computer system, perform a method of implementing a machine learning model for a detection of cancer in a biological sample, the method comprising:
sequencing nucleic acids of a human subject to obtain a set of sequence reads generated from a sample from the human subject, the set of sequence reads corresponding to a plurality of chromosomes;
storing definitions of a set of features to be input to the machine learning model, the set of features including non-aligned variables, the non-aligned variables including statistical measures of occurrence of Kmers of a Kmer database in the set of sequence reads;
analyzing the set of sequence reads to obtain a feature vector, wherein the feature vector comprises values of the set of features for the set of sequence reads, each element of the feature vector corresponding to a feature that includes one or more variables;
operating on the feature vector using parameters of the machine learning model to obtain an output label of the sample, wherein the output label comprises the detection of cancer for the sample; and
providing the output label.

27. The computer product of claim 26, wherein the set of features further includes aligned variables, the aligned variables including one or more properties of a set of sequence reads in windows of a reference genome.

* * * * *